United States Patent [19]

Suzuki

[11] Patent Number: 5,639,634
[45] Date of Patent: Jun. 17, 1997

[54] CADHERIN POLYNUCLEOTIDES

[75] Inventor: Shintaro Suzuki, Torrance, Calif.

[73] Assignee: Doheny Eye Institute, Los Angeles, Calif.

[21] Appl. No.: 332,643

[22] Filed: Nov. 1, 1994

Related U.S. Application Data

[63] Continuation of Ser. No. 872,643, Apr. 17, 1992, abandoned.
[51] Int. Cl.⁶ .................................................. C12N 15/12
[52] U.S. Cl. ...................... 435/69.1; 536/235; 435/240.2; 435/252.3; 435/254.11; 435/320.1
[58] Field of Search .......................... 435/69.1, 240.2, 435/320.1, 252.1, 254.11, 252.3; 536/23.1, 23.3, 23.5

[56] References Cited

FOREIGN PATENT DOCUMENTS

WO91/04745  4/1991  WIPO.

OTHER PUBLICATIONS

Jacobs et al., Nature, 313, 806, Feb. 1985.
Young et al., PNAS, 80, 1194, Mar. 1983.
Geiger et al., J. Cell Science, 97, 607, 1990.
Sambrook et al., "Molecular Cloning, A Laboratory Manual", pp. 16.2–16.31, Cold Spring Harbor Lab. Press, 1989.
Ausubel et al., Eds., Current Protocols in Molecular Biology, Sections, 6.1.1 to 6.1.4 and 6.2.1 to 6.2.3, John Wiley and Sons Ltd., New York (1987).
Behrens et al., J. Cell Biol., 108, 2435–2447 (1989).
Collins et al., J. Cell Biol., 113, 381–391 (1991).
Detrick et al., Neuron, 4, 493–506 (1990).
Donalies et al., Proc. Natl. Acad. Sci. USA, 88, 8024–8028 (1991).
Frixen et al., J. Cell Biol., 113, 173–185 (1991).
Gallin et al., Proc. Natl. Acad. Sci. USA, 84, 2808–2812 (1987).
Hatta et al., J. Cell Biol., 106, 873–881 (1988).
Heimark et al., J. Cell Biol., 110, 1745–1756 (1990).
Inuzuka et al., Neuron, 7, 69–79 (1991).
Klämbt et al., Devel. Biol., 133, 425–436 (1989).
Liaw et al., EMBO J., 9, 2701–2708 (1990).
Mahoney et al., Cell, 67, 853–868 (1991).
Maniatis et al., Eds., Molecular Cloning: A Laboratory Manual, p. 196, Cold Spring Harbor Laboratory, Cold Spring Harbor, New York (1982).
Matsunaga et al., Nature, 334, 62–64 (1988).
Nagafuchi et al., Nature, 329, 341–343 (1987).
Napolitano et al., J. Cell Biol., 113, 893–905 (1991).
Nose et al., EMBO J., 6, 3655–3661 (1987).
Ranscht et al., Neuron, 7, 391–402 (1991).
Ringwald et al., EMBO J., 6, 3647–3653 (1987).
Sacristan et al., J. Cell Biol., 111, Abstract 158a (1990).
Saiki et al., Science, 239, 487–491 (1988).
Suzuki et al., Cell Regulation, 2, 261–270 (1991).
Suzuki et al., J. Cell Biol., 115, Abstract 72a (1991).
Suzuki et al., Cell Struc. Func., 16, 605 (1991).
Takeichi, Science, 251, 1451–1455 (1991).
Takeichi, Annu. Rev. Biochem., 59, 237–252 (1990).
Tanihara et al., Invest. Ophthalmol. Vis. Sci., 32, 1013 (1991).
Thomas, Proc. Natl. Acad. Sci. USA, 77, 5201–5202 (1980).
Vleminckx et al., Cell, 66, 107–119 (1991).
Yoshida–Noro et al., Devel. Biol., 101, 19–27 (1984).

Primary Examiner—Stephen Walsh
Assistant Examiner—Sally P. Teng
Attorney, Agent, or Firm—Marshall, O'Toole, Gerstein, Murray & Borun

[57] ABSTRACT

DNA sequences encoding novel cadherins, desginated cadherins-4 through -13, are disclosed along with methods and materials for the recombinant production of the same. Antibody substances specific for the novel cadherins are disclosed as useful for affecting the natural binding and/or regulatory acitivities of the cadherins, for diagnosing tumors, and for targeted drug delivery.

15 Claims, No Drawings

CADHERIN POLYNUCLEOTIDES

This invention was made with government support under grant No. 5 R01 HL45335-04 awarded by the Heart, Lung and Blood Institute of the National Institutes of Health and grant No. 7 R01 CA42571 awarded by the National Cancer Institute of the National Institutes of Health. The government has certain rights in the invention.

This is a Rule 62 file wrapper continuation of U.S. application Ser. No. 07/872,643, filed Apr. 17, 1992, now abandoned.

FIELD OF THE INVENTION

The present invention relates, in general, to materials and methods relevant to cell-cell adhesion. More particularly, the invention relates to novel $Ca^{2+}$-dependent cell adhesion proteins, referred to as cadherins, and to polynucleotide sequences encoding the cadherins. The invention also relates to methods for inhibiting binding of the cadherins to their natural ligands/antiligands.

BACKGROUND

In vivo, cell-cell adhesion plays an important role in a wide range of events including morphogenesis and organ formation, leukocyte extravasion, tumor metastasis and invasion, and the formation of cell junctions. Additionally, cell-cell adhesion is crucial for the maintenance of tissue integrity, e.g., the maintenance of the intestinal epithelial barrier and the integrity of cardiac muscle.

Intercellular adhesion is mediated by specific cell adhesion molecules. Cell adhesion molecules have been classified into at least three superfamilies including the immunoglobulin (Ig) superfamily, the integrin superfamily and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain that determines binding specificity (the N-terminal 113 amino acids appear to be directly involved in binding), a hydrophobic membrane-spanning domain and a C-terminal cytoplasmic domain (highly conserved among the members of the superfamily) that interacts with the cytoskeleton through catenins and other cytoskeleton-associated proteins. Some cadherins lack a cytoplasmic domain, however, and appear to function in cell-cell adhesion by a different mechanism than cadherins that do have a cytoplasmic domain. The cytoplasmic domain is required for the binding function of the extracellular domain in cadherins that do have an intracellular domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59: 237–252 (1990) and Takeichi, *Science*, 251, 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvment in $Ca^{2+}$-dependent cell adhesion and their unique immunological characteristics and tissue localization. With the later immunological identification of N-cadherin, which was found to have a different tissue distribution from E-cadherin, it became apparent that a new family of $Ca^{2+}$-dependent cell-cell adhesion molecules had been discovered.

The molecular cloning of the genes encoding E-[see Nagafuchi et al., *Nature*, 329: 341–343 (1987)], N-[Hatta et al., *J. Cell Biol.*, 106: 873–881 (1988)], and P-[Nose et al., *EMBO J.* 6: 3655–3661 (1987)] cadherins provided structural evidence that the cadherins comprised a family of cell adhesion molecules. Cloning of L-CAM [Gallin et al., *Proc. Natl. Acad. Sci. USA*, 84: 2808–2812 (1987)] and uvomorulin [Ringwald et al., *EMBO J.*, 6: 3647–3653 (1987)] revealed that they were identical to E-cadherin. Comparisons of the amino acid sequences of E-, N-, and P-cadherins showed a level of amino acid similarity of about 45%–58% among the three subclasses. Liaw et al., *EMBO J.*, 9: 2701–2708 (1990) describes the use of PCR with degenerate oligonucleotides based on conserved regions of E-, N- and P-cadherins to isolate N- and P-cadherin from a bovine microvascular endothelial cell cDNA. The Liaw et al., supra, results implied that there were only E-, N-, and P-cadherins because no new cadherins were identified.

No further cadherin genes were described until the identification of eight of the novel cadherins claimed herein was reported in Suzuki et al., *Cell Regulation*, 2: 261–270 (1991). Subsequently, several other cadherins were described including R-cadherin [Inuzuka et al., *Neuron*, 7: 69–79 (1991)], M-cadherin [Donalies et al., *Proc. Natl. Acad. Sci. USA*, 88: 8024–8028 (1991)], B-cadherin [Napolitano et al., *J. Cell. Biol.*, 113: 893–905 (1991)], and T-cadherin [Ranscht et al., *Neuron*, 7: 391–402 (1991)].

The determinations of the tissue expression of the various cadherins reveals that each subclass of cadherins has a unique tissue distribution pattern. For example, E-cadherin is found in epithelial tissues while N-cadherin is found in nonepithelial tissues such as neural and muscle tissue. The unique expression pattern of the different cadherins is particularly significant when the role each subclass of cadherins may play in vivo in normal events (e.g., the maintenance of the intestinal epithelial barrier) and in abnormal events (e.g., tumor metastatis or inflammation) is considered. Different subclasses or combinations of subclasses of cadherins are likely to be responsible for different cell-cell adhesion events in which therapeutic detection and/or intervention may be desirable. Studies have also suggested that cadherins may have some regulatory activity in addition to adhesive activity. Matsunaga et al., *Nature*, 334, 62–64 (1988) reports that N-cadherin has neurite outgrowth promoting activity and Mahoney et al., *Cell*, 67, 853–868 (1991) reports that the Drosophila fat tumor supressor gene, another member of the cadherin superfamily, appear to regulate cell growth. Thus, therapeutic intervention in the regulatory activities of cadherins expressed in specific tissues may also be desirable.

There thus continues to exist a need in the art for the identification and characterization of additional cadherins participating in cell-cell adhesion and/or regulatory events. Moreover, to the extent that cadherins might form the basis for the development of therapeutic and diagnostic agents, it is essential that the genes encoding the proteins be cloned. Information about the DNA sequences and amino acid sequences encoding the cadherins would provide for the large scale production of the proteins and for the identification of the cells/tissues naturally producing the proteins, and would permit the preparation of antibody substances or other novel binding molecules specifically reactive with the cadherins that may be useful in affecting the natural ligand/antiligand binding reactions in which the cadherins are involved.

SUMMARY OF THE INVENTION

The present invention provides materials and methods that are relevant to cell-cell adhesion. In one of its aspects, the present invention provides purified and isolated polynucleotide sequences (e.g., DNA and RNA, both sense and antisense strands) encoding novel cadherins, cadherin-4 through -13. Preferred polynucleotide sequences of the invention include genomic and cDNA sequences as well as wholly or partially synthesized DNA sequences, and biological replicas thereof. Biologically active vectors comprising the polynucleotide sequences are also contemplated.

The scientific value of the information contributed through the disclosures of the DNA and amino acid sequences of the present invention is manifest. For example, knowledge of the sequence of a cDNA encoding a cadherin makes possible the isolation by DNA/DNA hybridization of genomic DNA sequences that encode the protein and that specify cadherin-specific expression regulating sequences such as promoters, enhancers and the like. DNA/DNA hybridization procedures utilizing the DNA sequences of the present invention also allow the isolation of DNAs encoding heterologous species proteins homologous to the rat and human cadherins specifically illustrated herein.

According to another aspect of the invention, host cells, especially eucaryotic and procaryotic cells, are stably transformed or transfected with the polynucleotide sequences of the invention in a manner allowing the expression of cadherin polypeptides in the cells. Host cells expressing cadherin polypeptide products, when grown in a suitable culture medium, are particularly useful for the large scale production of cadherin polypeptides, fragments and variants; thereby enabling the isolation of the desired polypeptide products from the cells or from the medium in which the cells are grown.

The novel cadherin proteins, fragments and variants of the invention may be obtained as isolates from natural tissue sources, but are preferably produced by recombinant procedures involving the host cells of the invention. The products may be obtained in fully or partially glycosylated, partially or wholly de-glycosylated or non-glycosylated forms, depending on the host cell selected or recombinant production and/or post-isolation processing.

Cadherin variants according to the invention may comprise polypeptide analogs wherein one or more of the specified (i.e., naturally encoded) amino acids is deleted or replaced or wherein one or more nonspecified amino acids are added: (1) without loss, and preferably with enhancement, of one or more of the biological activities or immunological characteristics specific for a cadherin; or (2) with specific disablement of a particular ligand/antiligand binding function of a cadherin.

Also contemplated by the present invention are antibody substances (e.g., monoclonal and polyclonal antibodies, chimeric and humanized antibodies, and antibody domains including Fab, Fab', F(ab')$_2$ and single chain domains, and Fv or single variable domains) which are specifically recognize a cadherins. Antibody substances can be developed using isolated natural, recombinant or synthetic cadherin polypeptide products or host cells expressing such products on their surfaces. The antibody substances may be utilized for purifying polypeptides of the invention, for determining the tissue expression of the polypeptides and as antagonists of the ligand/antiligand binding activities of the cadherins.

Numerous aspects and advantages of the present invention will be apparent upon consideration of the following detailed description thereof.

DETAILED DESCRIPTION

The present invention is illustrated by the following examples wherein Example 1 describes the isolation of cDNA sequences encoding rat cadherins-4 through -11 and -13; Example 2 describes the isolation of cDNA sequences encoding the human homologs of cadherins-4, -5, -6, -8, -10, -11 and -13 and the isolation of a human cadherin not identified in rat, cadherin-12; Example 3 describes the expression of cadherins-4 and -5 in mouse fibroblast L cells and an assay for the ability of the cadherins to mediate cell-cell adhesion; and Example 4 describes the generation of antibodies to cadherin-5. The disclosures of Suzuki et al., supra; Suzuki et al., *J. Cell. Biol.*, 115, Abstract 72a (1991); Suzuki et al., *Cell. Struc. Funct.*, 16, 605 (1991); and Tanihara et al., *Invest. Ophthalmol. Vis. Sci.*, 32, 1013 (1991) are incorporated by reference herein.

EXAMPLE 1 cDNA clones encoding nine novel cadherins were isolated from rat brain and retina by PCR. Eight of the novel cadherins cDNAs were isolated using degenerate PCR primers based on highly conserved regions of the cytoplasmic domain of known cadherins and one was isolated using degenerate PCR primers based on moderately conserved regions of the extracellular domain of known cadherins.

Preparation of Rat cDNA

Total RNAs were prepared from rat brain by the guanidium isothiocyanate/cesium chloride method described in Maniatis et al., pp. 196 in *Molecular Cloning: A Laboratory Manual*, Cold Spring Harbor, N.Y.: Cold Spring Harbor Laboratory (1982). Brain poly(A)$^+$ RNAs were then isolated using an Invitrogen (San Diego, Calif.) FastTrack kit. Rat retina poly(A)$^+$ RNA was purchased from Clonetech (Palo Alto, Calif.). cDNA was synthesized from the poly(A)$^+$ RNA of both rat brain and retina using a cDNA synthesis kit (Boehringer-Mannheim Corporation, Indianapolis, Ind.).

Design and Synthesis of PCR Primers Corresponding to Cadherin Cytoplasmic Domain A first pair of degenerate oligonucleotide primer sets, listed below in IUPAC nomenclature, were designed to correspond to highly conserved sequences in the cytoplasmic domain of the mouse N-, E-, and P-cadherins. Underlined sequences at the end of each oligonucleotide indicate an EcoR1 site added to the primers to facilitate cloning of the fragments generated by PCR.

Set 1
TAPPYD (SEQ ID NO: 1)
5' <u>GAATTC</u>ACNGCNCCNCCNTAYGA 3'   (SEQ ID NO: 2)

Set 2
FKKLAD (SEQ ID NO: 3)
3' AARTTYTTYRANCGNCT<u>CTTAAG</u> 5'   (SEQ ID NO: 4)

The degenerate oligonucleotides were synthesized using the Applied Biosystems model 380B DNA synthesizer (Foster City, Calif.).

Design and Synthesis of PCR Primers Corresponding to Cadherin Extracellular Domain A second pair of degenerate oligonucleotide primer sets, listed below in IUPAC nomenclature, were designed to correspond to moderately conserved sequences in the third repeat of the extracellular domain of the mouse N-, E-, and P-cadherins. The extracellular domains of the mouse N-, E- and P-cadherins have been characterized as having five internal repeating sequences that may be involved in cadherin interaction with $Ca^{2+}$. Underlined sequences at the end of each oligonucleotide indicate an EcoR1 site added to the primers to facilitate cloning of the fragments generated by PCR.

Set 3
K(P/G) (L/I/V)D(F/Y)E (SEQ ID NO: 5)
5' GAATTCAARS S NNTNGAYTWYGA 3' (SEQ ID NO: 6)

Set 4
(N/D)E(A/P)PXF (SEQ ID NO: 7)
3' TRCTYS GNGGNNNNAARCTT AAG 5' (SEQ ID NO: 8)

Cloning of cDNA Encoding Eight Novel Cadherins

PCR amplification reactions of rat brain and retina cDNA were carried out either with primer sets 1 and 2 or with primer sets 3 and 4 under conditions essentially the same as those described in Saiki et al., *Science*, 239, 487–491 (1988). Briefly, 100 ng of brain or retina cDNA was used as template for amplification with 10 μg of each primer set. PCR reactions were initiated by adding 2 units of Taq DNA polymerase (International Bioltechnology, New Haven, Conn.), to the reaction solution, after which 35 PCR reaction cycles were carried out. Reaction cycles consisted of denaturation performed at 94° C. for 1.5 minutes, oligonucleotide annealing at 45° C. for 2 minutes, and polymerization at 72° C. for 3 minutes. The resulting PCR fragments were separated by agarose gel electrophoresis, and DNA bands of the expected size were extracted from the gel and digested with EcoR1. The fragments were then cloned into the M13 vector (Boehringer Mannheim Corp., Indianapolis, Ind.) and *E. coli* JM101 cells were transformed with the resulting constructs. Individual clones were then isolated and sequenced. Sequencing of DNAs was carried out using a sequenase kit (United States Biochemicals, Cleveland, Ohio) and DNA and deduced amino acid sequences of the clones were compared to sequences of known cadherins using the Microgenie program (Beckman, Fullerton, Calif.).

Ten different types of cDNA clones encoding cadherins were identified from the PCR reaction based on primer sets 1 and 2. Two types of clones corresponded to rat N-, and E-cadherins, but eight types encoded previously undescribed cadherins, and were designated cadherins-4 through -11. The DNA and deduced amino acid sequences of the eight rat cDNA clones are respectively set out in SEQ ID NOs: 9 and 10 (cadherin-4), SEQ ID NOs: 11 and 12 (cadherin-5), SEQ ID NOs: 13 and 14 (cadherin-6), SEQ ID NOs: 15 and 16 (cadherin-7), SEQ ID NOs: 17 and 18 (cadherin-8), SEQ ID NOs: 19 and 20 (cadherin-9), SEQ ID NOs: 21 and 22 (cadherin-10) and SEQ ID NOs: 23 and 24 (cadherin-11).

An additional novel cadherin was identified from the PCR reaction based on primer sets 3 and 4, and it was designated cadherin-13. The DNA and deduced amino acid sequences of the rat cadherin-13 fragment are respectively set out in SEQ ID NOs: 25 and 26.

The PCR reaction based on primer set 3 and 4 also amplified sequences which were later determined to be fragments of the extracellular domains of rat cadherins-4, -5, -6, -8, -9, -10, -11. The DNA and amino acid sequences of these extracellular fragments are respectively set out in SEQ ID NOs: 27 and 28 (cadherin-4), SEQ ID NOs: 29 and 30 (cadherin-5), SEQ ID NOs: 31 and 32 (cadherin-6), SEQ ID NOs: 33 and 34 (cadherin-8), SEQ ID NOs: 35 and 36 (cadherin-9), SEQ ID NOs: 37 and 38 (cadherin-10), SEQ ID NOs: 39 and 40 (cadherin-11).

EXAMPLE 2

Full length cDNAs encoding human homologs of cadherins-4, -8, and -11 and partial cDNAs encoding human homologs of cadherins-5 and -10 were isolated from a human fetal brain cDNA library (λZapII vector, Stratagene, La Jolla, Calif.), and a full length cDNA encoding a human homologue of cadherin-5 was isolated from a human placental cDNA library (λgt11 vector, Dr. Millan, La Jolla Cancer Research Foundation, La Jolla, Calif.).

Synthesis of Probe Sequences

Probes for screening the human fetal brain and placental cDNA libraries were amplified by PCR from human brain cDNA (Dr. Taketani, Kansain Medical University, Moriguchi, Osaka, Japan) using the primers described in Example 1. Probes consisting of cadherin-4, -5, -6, -8, -10 and -11 sequences were generated using primer sets 1 and 2 and probes consisting of cadherin-13 sequence were generated using primer sets 3 and 4. Amplification of the human brain cDNA with primer sets 3 and 4 also generated a PCR fragment encoding a cadherin not isolated from rat, designated cadherin-12.

Isolation of Human Homologs

PCR fragments encoding cadherins-4, -5, -6, -8, -10, -11, -12 and -13 were labelled with $^{32}$P and used to probe the human fetal brain and placental cDNA libraries according to the plaque hybridization method described in Ausubel et al., Eds., *Current Protocols in Molecular Biology*, Sections 6.1.1 to 6.1.4 and 6.2.1 to 6.2.3, John Wiley & Sons, New York (1987). Positives were plaque-purified and inserts were cut out using an in vivo excision method. The inserts were then subcloned into the M13 vector (Boehringer Mannheim Corp.) for sequencing.

Inserts consisting of full length cDNAs encoding human homologs of cadherins-4, -8, -11, -12 and -13 and partial cDNAs encoding human homologs of cadherins-6 and -10 were identified in clones from the human fetal brain cDNA library and a full length cDNA encoding a human homologue of cadherin-5 was identified in a clone from the human placental cDNA library. The DNA and deduced amino acid sequences of the human homologs are respectively set out in SEQ ID NOs: 41 and 42 (cadherin-4), SEQ ID NOs: 43 and 44 (cadherin-5), SEQ ID NOs: 45 and 46 (cadherin-6), SEQ ID NOs: 47 and 48 (cadherin-8), SEQ ID NOs: 49 and 50 (cadherin-10), SEQ ID NOs: 51 and 52 (cadherin-11), SEQ ID NOs: 53 and 54 (cadherin-12), and SEQ ID NOs: 55 and 56 (cadherin-13).

EXAMPLE 3

To confirm that the cadherins of the present invention function as cell-cell adhesion molecules, cadherins-4 and -5 were expressed in mouse fibroblast L cells which normally do not express cell adhesion molecules. Adherence of L cells expressing the cadherin polypeptides of the invention indicates that the expression of the polypeptides confers $Ca^{2+}$-dependent intercellular binding activity.

Cell Adhesion Assay of Transfectants

The human cDNAs encoding cadherins-4 and -5 were subcloned into the multicloning site of expression vector pRC/RSV (Invitrogen, San Diego, Calif.).

Cadherin-4 DNA sequences were isolated by an in vivo excision procedure from the λZapII clone containing the entire coding sequence of cadherin-4 (described in Example 2). Using a helper virus, the sequences were excised from λZapII in the form of Bluescript plasmid. The plasmid was then cut with HindII and blunt-ended with T4 polymerase. The resulting DNA was fragment was redigested with SpeI to generate a cadherin-4 cDNA fragment having a blunt end and a SpeI sticky end. The fragment was purified by agarose gel electrophoresis and subcloned into pRC/RSV expression vector that had been previously digested with SpeI and XbaI (the XbaI end was blunt-ended with T4 polymerase).

The λgt11 clone containing the entire coding sequence of cadherin-5 (described in Example 2) was cut with EcoRI and the resulting fragment containing the cadherin-5 sequences was purified by agarose gel electrophoresis. The purified fragment was then subcloned into the EcoRI site of the Bluescript plasmid. Cadherin-5 sequences were cut from the resulting construct with HincIII and XbaI and subcloned into the NotI-XbaI site of the pRC/RSV vector.

Mouse fibroblast L cells were transfected with the cadherin-4 and -5 expression constructs by a $Ca^{2+}$ phosphate method and stable transfectants were obtained by G418 selection.

The cell-cell adhesion activity of the transfected cells was assayed by a re-aggregation assay described in Yoshida-Noro et al., Devel. Biol., 101, 19–27 (1984). Briefly, transfectants were grown to near confluency and then dispersed into single cells with mild trypsin treatment in the presence of $Ca^{2+}$. The trypsinized cell suspension was incubated on a rotary shaker at 50 rpm for 30 to 60 minutes and cell aggregation was monitored in the presence of $Ca^{2+}$.

Most of the transfected cells showed epithelial morphology and exhibited weak cell aggregation activity in the presence of $Ca^{2+}$, while control L cells transfected with only vector DNA and no cadherin DNA exhibited fibroblastic morphology and no significant cell aggregation activity.

EXAMPLE 4

The expression of mRNAs encoding cadherins of the invention was examined in rat brain, kidney, liver, lung and skin and in various human cells by Northern blot analysis.

Expression in Rat Tissue

Poly(A)$^+$ RNA from rat brain, kidney, liver, lung and skin was prepared as described in Example 1 for rat brain. The RNA preparations were then electrophoresed in an 0.8% agarose gel under denaturing conditions and transferred onto a nitrocellulose filter. Northern blot analyses were carried according to a method described in Thomas, Proc. Natl. Acad. Sci. USA, 77, 5201–5202 (1980). Filters were hybridized with rat cadherin PCR fragments (described in Example 1) labeled with $^{32}$P, including fragments corresponding to cadherins-4 through -11. The final hybridization wash was in 0.2×standard saline citrate containing 0.1% sodium dodecyl sulfate at 65° C. for 10 minutes.

mRNAs for cadherin-4 and cadherins-8 through -10 were detected only in rat brain. The cadherin-8 PCR fragment hybridized to multiple mRNA species that may be alternative splicing products. The sizes of the mRNAs detected were 3.5 to 5 kb, sizes similar to that encoding previously described cadherins. Cadherin-6 and -7 probes gave weak signals on brain mRNA even after prolonged exposure. mRNAs for cadherins-5, -6 and -11 were detected in rat tissues in addition to brain including cadherin-5 mRNA in lung and kidney, cadherin-6 mRNA in kidney, and cadherin-11 mRNA in liver.

Expression in Human Cells

Expression of cadherin-8 and -11 in cultured human neuroblastoma, glioma and retinoblastoma cells was also assayed by Northern blot. Human cDNAs encoding cadherins-8 and -11 (described in Example 2) were labelled with $^{32}$P and used as probes of poly(A)$^+$ RNA prepared from the cells using an Invitrogen FastTrack kit.

The Northern blot procedure detected cadherin-8 RNA in the neuroblastoma and retinoblastoma cell lines, while cadherin-11 RNA was detected only in neuroblastoma cells. These results indicate that at least some of the cadherins of the invention are expressed in neurons and glial cells and/or their precursor cells.

Cadherin-5 RNA was detected by Northern blot assay of endothelial cells from human umbilical cord vein (Clonetics, San Diego, Calif.), but was not detected in human epidermoid carcinoma cells or human fibroblast cells.

EXAMPLE 5

Antibodies to cadherin-5 were generated and tested by immunoblotting.

A cDNA fragment corresponding to a 40 KD portion (nucleotides 535 to 1527 of SEQ ID NO: 43) of the extracellular domain of cadherin-5 was synthesized by PCR from the full-length human cDNA described in Example 2 and was subcloned into the multicloning site (EcoR1-XbaI) of the pMAL-RI plasmid vector (New England Biolabs Inc., Beverly, Mass.). E. coli strain MNN522 cells (Stratagene, La Jolla, Calif.) were then transformed with the resultant plasmid and grown in quantity. After disruption of E. coli cells, the fusion protein was purified by affinity column chromatography using amylose resin (New England Biolabs Inc.) according to the instructions of the manufacturer and the resulting purified fusion protein showed essentially one band at 80 KD (40 KD cadherin-5+42,700 KD maltose binding protein).

500 µg of the cadherin-5 fusion protein in Freund's complete adjuvant was injected into rabbits each of four subcutaneous sites. Subsequent injections were carried out at three week intervals using 100 µg of the fusion protein in Freund's complete adjuvant again at each of four subcutaneous sites. The resulting polyclonal serum was collected.

Immunoblotting of various cell types showed that anti-cadherin-5 serum reacts with a 135 KD protein in L cells transfected with a full length cadherin-5 DNA and in human umbilical vein endothelial cells. The serum does not react with MDCK cells that express high levels of E-cadherin. In bovine aortic endothelial cells, the anti-cadherin-5 serum reacts with a protein of 120 KD. In addition, the anti-cadherin-5 serum reacts with rat brain endothelial cells in culture.

While the present invention has been described in terms of preferred embodiments, it is understood that variations and improvements will occur to those skilled in the art. Thus, only such limitations as appear in the appended claims should be placed on the scope of the invention.

What is claimed is:

1. A purified and isolated polynucleotide encoding a human cadherin selected from the group consisting of the cadherin-5 polypeptide of SEQ ID NO: 44, the cadherin-8 polypeptide of SEQ ID NO: 48, the cadherin-11 polypeptide of SEQ ID NO: 52, the cadherin-12 polypeptide of SEQ ID NO: 54 and the cadherin 13 polypeptide of SEQ ID NO: 56.

2. A purified and isolated polynucleotide encoding a rat cadherin, said cadherin comprising a polypeptide selected from the group consisting of: the cadherin-5 polypeptide of SEQ ID NO: 12 or SEQ ID NO: 30, the cadherin-8 polypeptide of SEQ ID NO: 18 or SEQ ID NO: 34, the cadherin-11 polypeptide of SEQ ID NO: 24 or SEQ ID NO: 40, and the cadherin-13 polypeptide of SEQ ID NO: 26.

3. The polynucleotide of claim 1 or 2, which is a DNA.

4. The polynucleotide of claim 3 which is a cDNA.

5. The cadherin-5 polynucleotide of claim 1 which is SEQ ID NO: 43.

6. The cadherin-8 polynucleotide of claim 1 which is SEQ ID NO: 47.

7. The cadherin-11 polynucleotide of claim 1 which is SEQ ID NO: 51.

8. The cadherin-12 polynucleotide of claim 1 which is SEQ ID NO: 53.

9. The cadherin-13 polynucleotide of claim 1 which is SEQ ID NO: 55.

10. The polynucleotide of claim 3 which is a genomic DNA.

11. The polynucleotide of claim 3 which is a wholly or partially chemically synthesized DNA.

12. A biologically functional DNA vector comprising a DNA according to claim 3.

13. The vector of claim 12 wherein said DNA is operatively linked to an expression control DNA sequence.

14. A host cell stably transformed or transfected with a DNA according to claim 3 in a manner allowing the expression in said host cell of the cadherin polypeptide encoded thereby.

15. A method for producing a cadherin polypeptide comprising the steps of growing a host cell according to claim 14 under conditions that allow expression of the cadherin polypeptide and isolating the cadherin from said cell or from the medium of its growth.

* * * * *

UNITED STATES PATENT AND TRADEMARK OFFICE
CERTIFICATE OF CORRECTION

PATENT NO. : 5,639,634

DATED : June 17, 1997

INVENTOR(S) : Shintaro Suzuki

It is certified that error appears in the above-identified patent and that said Letters Patent is hereby corrected as shown below:

Col. 1, line 23, "In vivo" should be --in vivo--.

Col. 2, line 16, "supra" should be --supra--.

Col. 2, line 35, "in vivo" should be --in vivo--.

Col. 2, line 46, "fat" should be --fat--.

Col. 4, line 8, "supra" should be --supra--.

Col. 4, line 22, "Preparation of Rat cDNA" should be --Preparation of Rat cDNA--.

Col. 4, lines 34-35, "Design and Synthesis of PCR Primers Corresponding to Cadherin Cytoplasmic Domain" should be --Design and Synthesis of PCR Primers Corresponding to Cadherin Cytoplasmic Domain--.

Col. 4, line 41, "EcoR1" should be --EcoR1--.

Col. 4, lines 56-57, "Design and Synthesis of PCR Primers Corresponding to Cadherin Extracellular Domain" should be --Design and Synthesis of PCR Primers Corresponding to Cadherin Extracellular Domain--.

Col. 4, line 66, "EcoR1" should be --EcoR1--.

Col. 5, line 4, "5'GAATTCAARSS..." should be --5'GAATTCAARSS...--.

Col. 5, line 11 "Cloning of cDNA Encoding Eight Novel Cadherins" should be --Cloning of cDNA Encoding Eight Novel Cadherins--.

Col. 5, line 27, "EcoR1" should be --EcoR1--.

UNITED STATES PATENT AND TRADEMARK OFFICE
CERTIFICATE OF CORRECTION

PATENT NO. : 5,639,634

DATED : June 17, 1997

INVENTOR(S) : Shintaro Suzuki

It is certified that error appears in the above-identified patent and that said Letters Patent is hereby corrected as shown below:

Col. 5, line 56, "-6, -8, -9, -10, -11." should be -- -6, -8, -9, -10, and -11.--.

Col. 6, line 5, "Synthesis of Probe Sequences" should be --Synthesis of Probe Sequences--.

Col. 6, line 17, "Isolation of Human Homologs" should be --Isolation of Human Homologs--.

Col. 6, line 25, "in vivo" should be --in vivo--.

Col. 6, line 50, "Cell Adhesion Assay of Transfectants" should be --Cell Adhesion Assay of Transfectants--.

Col. 6, line 54, "in vivo" should be --in vivo--.

Col. 6, line 59, "HindII" should be --HindII--.

Col. 6, line 60, "SpeI" should be --SpeI--.

Col. 6, line 62, "SpeI" should be --SpeI--.

Col. 6, line 64, "SpeI and XbaI" should be --SpeI and XbaI--.

Col. 6, line 65, "XbaI" should be --XbaI--.

Col. 6, line 67, "EcoRI" should be --EcoRI--.

Col. 7, line 3, "EcoRI" should be --EcoRI--.

Col. 7, line 5, "HincIII and xbaI" should be --HincIII and XbaI--.

Col. 7, line 6, "NotI-XbaI" should be --NotI-XbaI--.

Col. 7, line 30, "Expression in Rat Tissue" should be --Expression in Rat Tissue--.

Col. 7, line 54, "Expression in Human Cells" should be --Expression in Human Cells--.

UNITED STATES PATENT AND TRADEMARK OFFICE
CERTIFICATE OF CORRECTION

PATENT NO. : 5,639,634
DATED : June 17, 1997
INVENTOR(S) : Shintaro Suzuki

It is certified that error appears in the above-identified patent and that said Letters Patent is hereby corrected as shown below:

Col. 8, line 24, "(EcoR1-Xba1)" should be --(EcoR1 - Xba1)--.

Signed and Sealed this

Tenth Day of February, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:1:

Thr  Ala  Pro  Pro  Tyr  Asp
        1                 5

( 2 ) INFORMATION FOR SEQ ID NO:2:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:2:

GAATTCACNG CNCCNCCNTA Y GA                                                                            23

( 2 ) INFORMATION FOR SEQ ID NO:3:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:3:

Phe  Lys  Lys  Leu  Ala  Asp
        1                 5

( 2 ) INFORMATION FOR SEQ ID NO:4:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:4:

GAATTCTCNG CNAR YTT Y TT RAA                                                                          23

( 2 ) INFORMATION FOR SEQ ID NO:5:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 2
                ( D ) OTHER INFORMATION: /note= "The amino acid at this
                        position is a proline or a glycine."

( i x ) FEATURE:
                ( A ) NAME/KEY: Modified-site
                ( B ) LOCATION: 3
                ( D ) OTHER INFORMATION: /note= "The amino acid at this
                        position is a leucine, an isoleucine or a valine."

( i x ) FEATURE:

(A) NAME/KEY: Modified-site
(B) LOCATION: 5
(D) OTHER INFORMATION: /note= "The amino acid at this position is a phenylalanine or a tyrosine."

(xi) SEQUENCE DESCRIPTION: SEQ ID NO:5:

Lys Xaa Xaa Asp Xaa Glu
1               5

(2) INFORMATION FOR SEQ ID NO:6:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:6:

GAATTCAARS SNNTNGAYTW YGA    23

(2) INFORMATION FOR SEQ ID NO:7:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "The amino acid at this position is an asparagine or an aspartic acid."

(ix) FEATURE:
    (A) NAME/KEY: Modified-site
    (B) LOCATION: 3
    (D) OTHER INFORMATION: /note= "The amino acid at this position is an alanine or a proline."

(xi) SEQUENCE DESCRIPTION: SEQ ID NO:7:

Xaa Glu Xaa Pro Xaa Phe
1               5

(2) INFORMATION FOR SEQ ID NO:8:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:8:

GAATTCRAAN NNNGGNGSYT CRT    23

(2) INFORMATION FOR SEQ ID NO:9:

(i) SEQUENCE CHARACTERISTICS:
    (A) LENGTH: 117 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:9:

```
TCCCTGCTGG TCTTCGACTA CGAAGGCAGC GGTTCTACTG CAGGCTCTGT CAGCTCCCTG    60

AACTCCTCCA GCTCCGGGGA TCAAGATTAC GACTACTTGA ATGACTGGGG GCCCCGG     117
```

( 2 ) INFORMATION FOR SEQ ID NO:10:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser Leu Leu Val Phe Asp Tyr Glu Gly Ser Gly Ser Thr Ala Gly Ser
 1               5                  10                  15

Val Ser Ser Leu Asn Ser Ser Ser Gly Asp Gln Asp Tyr Asp Tyr
            20                  25                  30

Leu Asn Asp Trp Gly Pro Arg
            35
```

( 2 ) INFORMATION FOR SEQ ID NO:11:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
ACACTGCACA TCTACGGCTA CGAGGGCACA GAGTCCATCG CAGAGTCCCT CAGCTCCCTG    60

AGCACCAATT CCTCCGACTC TGACATCGAC TATGACTTCC TCAATGACTG GGGACCCAGG   120
```

( 2 ) INFORMATION FOR SEQ ID NO:12:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Thr Leu His Ile Tyr Gly Tyr Glu Gly Thr Glu Ser Ile Ala Glu Ser
 1               5                  10                  15

Leu Ser Ser Leu Ser Thr Asn Ser Ser Asp Ser Asp Ile Asp Tyr Asp
            20                  25                  30

Phe Leu Asn Asp Trp Gly Pro Arg
            35                  40
```

( 2 ) INFORMATION FOR SEQ ID NO:13:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
TCCTTGGCCA CCTATGCCTA CGAAGGAACT GGCTCGGTGG CCGACTCCCT GAGCTCACTA    60

GAATCAGTGA CCACAGATGG AGACCAAGAT TATGACTATT TGAGTGACTG GGGCCCTCGA   120
```

( 2 ) INFORMATION FOR SEQ ID NO:14:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Ser Leu Ala Thr Tyr Ala Tyr Glu Gly Thr Gly Ser Val Ala Asp Ser
1                5                  10                 15
Leu Ser Ser Leu Glu Ser Val Thr Thr Asp Gly Asp Gln Asp Tyr Asp
            20                  25                 30
Tyr Leu Ser Asp Trp Gly Pro Arg
            35              40
```

( 2 ) INFORMATION FOR SEQ ID NO:15:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
TCGCTTCAGA CTTATGCATT TGAAGGAAAT GGCTCAGTAG CTGAATCTCT CAGTTCTTTA      60
GATTCTAACA GCTCGAACTC TGATCAGAAT TATGACTACC TTAGTGACTG GGGTCCTCTC     120
```

( 2 ) INFORMATION FOR SEQ ID NO:16:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ser Leu Gln Thr Tyr Ala Phe Glu Gly Asn Gly Ser Val Ala Glu Ser
1                5                  10                 15
Leu Ser Ser Leu Asp Ser Asn Ser Ser Asn Ser Asp Gln Asn Tyr Asp
            20                  25                 30
Tyr Leu Ser Asp Trp Gly Pro Arg
            35              40
```

( 2 ) INFORMATION FOR SEQ ID NO:17:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
TCCATTCAGA TTTATGGCTA TGAAGGCCGA GGGTCTGTGG CTGGCTCTCT CAGCTCGTTG      60
GAGTCCACCA CATCAGACTC AGACCAGAAT TTTGACTACC TCAGTGACTG GGGTCCCCGC     120
```

( 2 ) INFORMATION FOR SEQ ID NO:18:

( i ) SEQUENCE CHARACTERISTICS:

(A) LENGTH: 40 amino acids
(B) TYPE: amino acid
(D) TOPOLOGY: linear (ii) MOLECULE TYPE: protein (xi) SEQUENCE DESCRIPTION: SEQ ID NO:18:

| Ser | Ile | Gln | Ile | Tyr | Gly | Tyr | Glu | Gly | Arg | Gly | Ser | Val | Ala | Gly | Ser |
|---|---|---|---|---|---|---|---|---|---|---|---|---|---|---|---|
| 1 | | | | 5 | | | | | 10 | | | | | 15 | |

| Leu | Ser | Ser | Leu | Glu | Ser | Thr | Thr | Ser | Asp | Ser | Asp | Gln | Asn | Phe | Asp |
|---|---|---|---|---|---|---|---|---|---|---|---|---|---|---|---|
| | | | 20 | | | | 25 | | | | | 30 | | | |

| Tyr | Leu | Ser | Asp | Trp | Gly | Pro | Arg |
|---|---|---|---|---|---|---|---|
| | | 35 | | | | | 40 |

(2) INFORMATION FOR SEQ ID NO:19:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

TCCTTGGCCA CTTACGCCTA TGAAGGGAAT GATTCTGTAG CCAATTCTCT CAGCTCCTTA 60

GAATCTCTCA CAGCTGATTG TACCCAGGAT TATGACTACC TTAGTGACTG GGGGCCACGC 120

(2) INFORMATION FOR SEQ ID NO:20:

(i) SEQUENCE CHARACTERISTICS:
(A) LENGTH: 40 amino acids
(B) TYPE: amino acid
(D) TOPOLOGY: linear (ii) MOLECULE TYPE: protein (xi) SEQUENCE DESCRIPTION: SEQ ID NO:20:

| Ser | Leu | Ala | Thr | Tyr | Ala | Tyr | Glu | Gly | Asn | Asp | Ser | Val | Ala | Asn | Ser |
|---|---|---|---|---|---|---|---|---|---|---|---|---|---|---|---|
| 1 | | | | 5 | | | | | 10 | | | | | 15 | |

| Leu | Ser | Ser | Leu | Glu | Ser | Leu | Thr | Ala | Asp | Cys | Asn | Gln | Asp | Tyr | Asp |
|---|---|---|---|---|---|---|---|---|---|---|---|---|---|---|---|
| | | | 20 | | | | 25 | | | | | 30 | | | |

| Tyr | Leu | Ser | Asp | Trp | Gly | Pro | Arg |
|---|---|---|---|---|---|---|---|
| | | 35 | | | | | 40 |

(2) INFORMATION FOR SEQ ID NO:21:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:21:

TCGCTGGCTA CCTATGCCTA TGAAGGAAAC GACTCTGTTG CTAATCTCT GAGCTCCTTA 60

GAATCAGGTA CCACTGAAGG AGACCAAAAC TACGATTACC TTCGAGAATG GGGGCCTCGG 120

(2) INFORMATION FOR SEQ ID NO:22:

(i) SEQUENCE CHARACTERISTICS:
(A) LENGTH: 40 amino acids
(B) TYPE: amino acid
(D) TOPOLOGY: linear ( i i ) MOLECULE TYPE: protein ( x i ) SEQUENCE DESCRIPTION: SEQ ID NO:22:

```
Ser Leu Ala Thr Tyr Ala Tyr Glu Gly Asn Asp Ser Val Ala Glu Ser
1               5                   10                  15

Leu Ser Ser Leu Glu Ser Gly Thr Thr Glu Gly Asp Gln Asn Tyr Asp
                20                  25                  30

Tyr Leu Arg Glu Trp Gly Pro Arg
            35              40
```

( 2 ) INFORMATION FOR SEQ ID NO:23:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
TCCATCCAAA TCTATGGTTA TGAGGGCAGG GGTTCCGTGG CTGGGTCCCT GAGCTCCTTG      60
GAGTCTGCCA CCACAGATTC GGACCTGGAC TACGACTATC TACAGAACTG GGGACCTCGG     120
```

( 2 ) INFORMATION FOR SEQ ID NO:24:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Ser Ile Gln Ile Tyr Gly Tyr Glu Gly Arg Gly Ser Val Ala Gly Ser
1               5                   10                  15

Leu Ser Ser Leu Glu Ser Ala Thr Thr Asp Ser Asp Leu Asp Tyr Asp
                20                  25                  30

Tyr Leu Gln Asn Trp Gly Pro Arg
            35              40
```

( 2 ) INFORMATION FOR SEQ ID NO:25:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
AAGCGGTTTG ATTACGAGAT CTCTGCCTTT CACACCCTGC TGATCAAAGT GGAGAATGAG      60
GACCCATTGG TACCCGACGT CTCCTATGGC CCCAGCTCCA CGGCCACTGT CCACATCACG     120
GTCTTGGATG TCAACGAGGG ACCAGTCTTC                                       150
```

( 2 ) INFORMATION FOR SEQ ID NO:26:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Lys Arg Phe Asp Tyr Glu Ile Ser Ala Phe His Thr Leu Leu Ile Lys
1               5                   10                  15

Val Glu Asn Glu Asp Pro Leu Val Pro Asp Val Ser Tyr Gly Pro Ser
                20                  25                  30

Ser Thr Ala Thr Val His Ile Thr Val Leu Asp Val Asn Glu Gly Pro
            35                  40                  45

Val Phe
    50
```

( 2 ) INFORMATION FOR SEQ ID NO:27:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
AAGGGTATGG ATTATGAGCT GAACCGTGCC TCCATGCTGA CCATAATGGT GTCCAACCAG      60

GCGCCCCTGG CCAGCGGGAT CCAGATGTCC TTCCAGTCCA CAGTGGGGGT AACCATCTCT     120

GTCACCGATG TCAACGAAGC CCCCTACTTC                                      150
```

( 2 ) INFORMATION FOR SEQ ID NO:28:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Lys Gly Met Asp Tyr Glu Leu Asn Arg Ala Ser Met Leu Thr Ile Met
1               5                   10                  15

Val Ser Asn Gln Ala Pro Leu Ala Ser Gly Ile Gln Met Ser Phe Gln
                20                  25                  30

Ser Thr Val Gly Val Thr Ile Ser Val Thr Asp Val Asn Glu Ala Pro
            35                  40                  45

Tyr Phe
    50
```

( 2 ) INFORMATION FOR SEQ ID NO:29:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
AAACGACTGG ATTTGAACT CATCCAGCAG TACACGTTCC ACATCGAGGC CACAGACCCC       60

ACTATCAGAC TCGGATACCT GAGCAGCACT GCGGGCAAAA ACAAAGCCAA GATCATCATC     120

AATGTCCTAG ATGTGGATGA GCCCCCTGTT TTC                                  153
```

( 2 ) INFORMATION FOR SEQ ID NO:30:

( i ) SEQUENCE CHARACTERISTICS:

(A) LENGTH: 51 amino acids
(B) TYPE: amino acid
(D) TOPOLOGY: linear (ii) MOLECULE TYPE: protein (xi) SEQUENCE DESCRIPTION: SEQ ID NO:30:

```
Lys Arg Leu Asp Phe Glu Leu Ile Gln Gln Tyr Thr Phe His Ile Glu
 1               5                  10                  15
Ala Thr Asp Pro Thr Ile Arg Leu Gly Tyr Leu Ser Ser Thr Ala Gly
             20                  25                  30
Lys Asn Lys Ala Lys Ile Ile Ile Asn Val Leu Asp Val Asp Glu Pro
             35                  40                  45
Pro Val Phe
         50
```

(2) INFORMATION FOR SEQ ID NO:31:

(i) SEQUENCE CHARACTERISTICS:
(A) LENGTH: 153 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:31:

```
AAGGGTTTGG ATTTTGAAAA GAAGAAAGTG TATACCCTTA AAGTGGAAGC CTCCAATCCT      60
TATGTTGAGC CACGATTTCT CTACTTGGGG CCTTTCAAAG ATTCAGCCAC GGTTAGAATT     120
GTGGTGGAGG ATGTAGATGA ACCTCCTGCC TTC                                  153
```

(2) INFORMATION FOR SEQ ID NO:32:

(i) SEQUENCE CHARACTERISTICS:
(A) LENGTH: 51 amino acids
(B) TYPE: amino acid
(D) TOPOLOGY: linear (ii) MOLECULE TYPE: protein (xi) SEQUENCE DESCRIPTION: SEQ ID NO:32:

```
Lys Gly Leu Asp Phe Glu Lys Lys Lys Val Tyr Thr Leu Lys Val Glu
 1               5                  10                  15
Ala Ser Asn Pro Tyr Val Glu Pro Arg Phe Leu Tyr Leu Gly Pro Phe
             20                  25                  30
Lys Asp Ser Ala Thr Val Arg Ile Val Val Glu Asp Val Asp Glu Pro
             35                  40                  45
Pro Ala Phe
         50
```

(2) INFORMATION FOR SEQ ID NO:33:

(i) SEQUENCE CHARACTERISTICS:
(A) LENGTH: 153 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:33:

```
AAGCCTCTGG ACTTTGAGAC CAAAAAATCC TATACTCTGA AGGTGGAGGC AGCCAATATC      60
CACATCGACC CACGTTCAG TGGCAGGGGA CCCTTTAAAG ATACAGCAAC AGTCAAAATT     120
```

```
GTTGTAGAGG ATGCTGATGA GCCTCCGGTC TTC                                        153
```

( 2 ) INFORMATION FOR SEQ ID NO:34:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Asp Ala Leu Asp Phe Glu Thr Lys Lys Ser Tyr Thr Leu Lys Val Glu
1               5                   10                  15

Ala Ala Asn Ile His Ile Asp Pro Arg Phe Ser Gly Arg Gly Pro Phe
            20                  25                  30

Lys Asp Thr Ala Thr Val Lys Ile Val Val Glu Asp Ala Asp Glu Pro
            35                  40                  45

Pro Val Phe
        50
```

( 2 ) INFORMATION FOR SEQ ID NO:35:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AAGGGGGTGG ACTATGAAGC CAAAACAAGT TATACCCTGC GCATAGAAGC TGCAAATCGA        60
GATGCTGATC CCCGGTTTCT GAGCTTGGGT CCATTCAGTG ACACAACAAC AGTTAAGATA       120
ATTGTGGAAG ACGTGGATGA ACCCCCGTACT C                                     152
```

( 2 ) INFORMATION FOR SEQ ID NO:36:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Lys Gly Val Asp Tyr Glu Ala Lys Thr Ser Tyr Thr Leu Arg Ile Glu
1               5                   10                  15

Ala Ala Asn Arg Asp Ala Asp Pro Arg Phe Leu Ser Leu Gly Pro Phe
            20                  25                  30

Ser Asp Thr Thr Thr Val Lys Ile Ile Val Glu Asp Val Asp Glu Pro
            35                  40                  45

Pro Tyr Ser
        50
```

( 2 ) INFORMATION FOR SEQ ID NO:37:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

AAGCCACTTG ACTATGAGAA CCGAAGACTA TATACACTGA AGGTGGAGGC AGAAAATACC 60

CATGTGGATC CACGTTTTTA CTATTTAGGG CCATTCAAAG ATACAACAAT TGTAAAAATC 120

TCCATAGAAG ACGTGGATGA GCCACCCCCC TTT 153

( 2 ) INFORMATION FOR SEQ ID NO:38:

( i ) SEQUENCE CHARACTERISTICS:
( A ) LENGTH: 51 amino acids
( B ) TYPE: amino acid
( D ) TOPOLOGY: linear ( i i ) MOLECULE TYPE: protein ( x i ) SEQUENCE DESCRIPTION: SEQ ID NO:38:

```
Lys Pro Leu Asp Tyr Glu Asn Arg Arg Leu Tyr Thr Leu Lys Val Glu
 1               5                  10                  15

Ala Glu Asn Thr His Val Asp Pro Arg Phe Tyr Tyr Leu Gly Pro Phe
                20                  25                  30

Lys Asp Thr Thr Ile Val Lys Ile Ser Ile Glu Asp Val Asp Glu Pro
                35                  40                  45

Pro Pro Phe
        50
```

( 2 ) INFORMATION FOR SEQ ID NO:39:

( i ) SEQUENCE CHARACTERISTICS:
( A ) LENGTH: 153 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:39:

AGGGGTGTGG ATTATGAAAC CAAAAGAGCA TATAGCTTGA AGGTAGAGGC GGCCAATGTA 60

CACATTGATC CGAAGTTCAT CAGCAATGGA CCTTTCAAGG ACACAGTGAC TGTCAAGATT 120

GCAGTAGAAG ATGCCAATGA GCCCCCTCCC TTC 153

( 2 ) INFORMATION FOR SEQ ID NO:40:

( i ) SEQUENCE CHARACTERISTICS:
( A ) LENGTH: 51 amino acids
( B ) TYPE: amino acid
( D ) TOPOLOGY: linear ( i i ) MOLECULE TYPE: protein ( x i ) SEQUENCE DESCRIPTION: SEQ ID NO:40:

```
Arg Gly Val Asp Tyr Glu Thr Lys Arg Ala Tyr Ser Leu Lys Val Glu
 1               5                  10                  15

Ala Ala Asn Val His Ile Asp Pro Lys Phe Ile Ser Asn Gly Pro Phe
                20                  25                  30

Lys Asp Thr Val Thr Val Lys Ile Ala Val Glu Asp Ala Asn Glu Pro
                35                  40                  45

Pro Pro Phe
        50
```

( 2 ) INFORMATION FOR SEQ ID NO:41:

( i ) SEQUENCE CHARACTERISTICS:
( A ) LENGTH: 3048 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:41:

```
CGCCGGCGGG GAAGATGACC GCGGGCGCCG GCGTGCTCCT TCTGCTGCTC TCGCTCTCCG      60
GCGCGCTCCG GGCCCATAAT GAGGATCTTA CAACTAGAGA GACCTGCAAG GCTGGGTTCT     120
CTGAAGATGA TTACACGGCA TTAATCTCCC AAAATATTCT AGAAGGGGAA AAGCTACTTC     180
AAGTCAAGTT CAGCAGCTGT GTGGGGACCA AGGGGACACA ATATGAGACC AACAGCATGG     240
ACTTCAAAGT TGGGGCAGAT GGGACAGTCT TCGCCACCCG GGAGCTGCAG GTCCCCTCCG     300
AGCAGGTGGC GTTCACGGTG ACTGCATGGG ACAGCCAGAC AGCAGAGAAA TGGGACGCCG     360
TGGTGCGGTT GCTGGTGGCC CAGACCTCGT CCCCGCACTC TGGACACAAG CCGCAGAAAG     420
GAAAGAAGGT CGTGGCTCTG GACCCCTCTC CGCCTCCGAA GGACACCCTG CTGCCGTGGC     480
CCCAGCACCA GAACGCCAAC GGGCTGAGGC GGCGCAAACG GGACTGGGTC ATCCCACCCA     540
TCAACGTGCC CGAGAACTCG CGCGGGCCCT TCCCGCAGCA GCTCGTGAGG ATCCGGTCCG     600
ACAAAGACAA TGACATCCCC ATCCGGTACA GCATCACGGG AGTGGGTGCC GACCAGCCCC     660
CCATGGAGGT CTTCAGCATT AACTCCATGT CCGGCCGGAT GTACGTCACA AGGCCCATGG     720
ACCGGGAGGA GCACGCCTCT TACCACCTCC GAGCCCACGC TGTGGACATG AATGGCAACA     780
AGGTGGAGAA CCCCATCGAC CTGTACATCT ACGTCATCGA CATGAATGAC AACCACCCTG     840
AGTTCATCAA CCAGGTCTAC AACTGCTCCG TGGACGAGGG CTCCAAGCCA GGCACCTACG     900
TGATGACCAT CACGGCCAAC GATGCTGACG ACAGCACCAC GGCCAACGGG ATGGTGCGGT     960
ACCGGATCGT GACCCAGACC CCACAGAGCC CGTCCAGAA TATGTTCACC ATCAACAGCG    1020
AGACTGGAGA TATCGTCACA GTGGCGGCTG GCTGGGACCG AGAGAAAGTT CAGCAGTACA    1080
CAGTCATCGT TCAGGCCACA GATATGGAAG GAAATCTCAA CTATGGCCTC TCAAACACAG    1140
CCACAGCCAT CATCACGGTG ACAGATGTGA ATGACAACCC GTCAGAATTT ACCGCCAGCA    1200
CGTTTGCAGG GGAGGTCCCC GAAAACAGCG TGGAGACCGT GGTCGCAAAC CTCACGGTGA    1260
TGGACCGAGA TCAGCCCCAC TCTCCAAACT GGAATGCCGT TACCGCATC ATCAGTGGGG    1320
ATCCATCCGG GCACTTCAGC GTCCGCACAG ACCCCGTAAC CAACGAGGGC ATGGTCACCG    1380
TGGTGAAGGC AGTCGACTAC GAGCTCAACA GAGCTTTCAT GCTGACAGTG ATGGTGTCCA    1440
ACCAGGCGCC CCTGGCCAGC GGAATCCAGA TGTCCTTCCA GTCCACGGCA GGGGTGACCA    1500
TCTCCATCAT GGACATCAAC GAGGCTCCCT ACTTCCCCTC AAACCACAAG CTGATCCGCC    1560
TGGAGGAGGG CGTGCCCCCC GGCACCGTGC TGACCACGTT TCAGCTGTG GACCCTGACC    1620
GGTTCATGCA GCAGGCTGTG AGATACTCAA AGCTGTCAGA CCCAGCGAGC TGGCTGCACA    1680
TCAATGCCAC CAACGGCCAG ATCACCACGG TGGCAGTGCT GGACCGTGAG TCCCTCTACA    1740
CCAAAAACAA CGTCTACGAG GCCACCTTCC TGGCAGCTGA CAATGGGATA CCCCCGGCCA    1800
GCGGCACCGG GACCCTCCAG ATCTATCTCA TTGACATCAA CGACAACGCC CCTGAGCTGC    1860
TGCCCAAGGA GGCGCAGATC TGCGAGAGGC CCAACCTGAA CGCCATCAAC ATCACGGCGG    1920
CCGACGCTGA CGTGCACCCC AACATCGGCC CCTACGTCTT CGAGCTGCCC TTTGTCCCGG    1980
CGGCCGTGCG GAAGAACTGG ACCATCACCC GCCTGAACGG TGACTATGCC CAACTCAGCT    2040
TGCGCATCCT GTACCTGGAG GCCGGGATGT ATGACGTCCC CATCATCGTC ACAGACTCTG    2100
GAAACCCTCC CCTGTCCAAC ACGTCCATCA TCAAAGTCAA GGTGTGCCCA TGTGATGACA    2160
```

```
ACGGGGACTG CACCACCATT GGCGCAGTGG CAGCGGCTGG TCTGGGCACC GGTGCCATCG    2220

TGGCCATCCT CATCTGCATC CTCATCCTGC TGACCATGGT CCTGCTGTTT GTCATGTGGA    2280

TGAAGCGGCG AGAGAAGGAG CGCCACACGA AGCAGCTGCT CATTGACCCC GAGGACGACG    2340

TCCGCGAAAA GATCCTCAAG TATGACGAGG AAGGCGGTGG CGAGGAGGAC CAGGACTACG    2400

ACCTCAGCCA GCTGCAGCAG CCGGAAGCCA TGGGGCACGT GCCAAGCAAA GCCCCTGGCG    2460

TGCGTCGCGT GGATGAGCGG CCGGTGGGCC CTGAGCCCCA GTACCCGATC AGGCCCATGG    2520

TGCCGCACCC AGGCGACATC GGTGACTTCA TCAATGAGGG ACTCCGCGCT GCTGACAACG    2580

ACCCCACGGC ACCCCCCTAT GACTCCCTGC TGGTCTTCGA CTACGAGGGG AGCGGCTCCA    2640

CCGCAGGCTC CGTCAGCTCC CTGAACTCAT CCAGTTCCGG GGACCAAGAC TACGATTACC    2700

TCAACGACTG GGGCCCCAGA TTCAAGAAGC TGGCGGACAT GTATGGAGGT GGTGAAGAGG    2760

ATTGACTGAC CTCGCATCTT CGGACCGAAG TGAGAGCCGT GCTCGGACGC CGGAGGAGCA    2820

GGACTGAGCA GAGGCGGCCG GTCTTCCCGA CTCCCTGCGG CTGTGTCCTT AGTGCTGTTA    2880

GGAGGCCCCC CAATCCCCAC GTTGAGCTGT CTAGCATGAG CACCCACCCC CACAGCGCCC    2940

TGCACCCGGC CGCTGCCCAG CACCGCGCTG GCTGGCACTG AAGGACAGCA AGAGGCACTC    3000

TGTCTTCACT TGAATTTCCT AGAACAGAAG CACTGTTTTT AAAAAAAG                 3048
```

(2) INFORMATION FOR SEQ ID NO:42:

(i) SEQUENCE CHARACTERISTICS:
        (A) LENGTH: 916 amino acids
        (B) TYPE: amino acid
        (D) TOPOLOGY: linear (ii) MOLECULE TYPE: protein (xi) SEQUENCE DESCRIPTION: SEQ ID NO:42:

```
Met Thr Ala Gly Ala Gly Val Leu Leu Leu Leu Ser Leu Ser Gly
 1               5                  10                  15

Ala Leu Arg Ala His Asn Glu Asp Leu Thr Thr Arg Glu Thr Cys Lys
                20                  25                  30

Ala Gly Phe Ser Glu Asp Asp Tyr Thr Ala Leu Ile Ser Gln Asn Ile
            35                  40                  45

Leu Glu Gly Glu Lys Leu Leu Gln Val Lys Phe Ser Ser Cys Val Gly
        50                  55                  60

Thr Lys Gly Thr Gln Tyr Glu Thr Asn Ser Met Asp Phe Leu Val Gly
65                  70                  75                  80

Ala Asp Gly Thr Val Phe Ala Thr Arg Glu Leu Gln Val Pro Ser Glu
                85                  90                  95

Gln Val Ala Phe Thr Val Thr Ala Trp Asp Ser Gln Thr Ala Glu Lys
            100                 105                 110

Trp Asp Ala Val Val Arg Leu Leu Val Ala Gln Thr Ser Ser Pro His
        115                 120                 125

Ser Gly His Lys Pro Gln Lys Gly Lys Lys Val Val Ala Leu Asp Pro
    130                 135                 140

Ser Pro Pro Lys Asp Thr Leu Leu Pro Trp Pro Gln His Gln Asn
145                 150                 155                 160

Ala Asn Gly Leu Arg Arg Arg Lys Arg Asp Trp Val Ile Pro Pro Ile
                165                 170                 175

Asn Val Pro Glu Asn Ser Arg Gly Pro Phe Pro Gln Gln Leu Val Arg
            180                 185                 190

Ile Arg Ser Asp Lys Asp Asn Asp Ile Pro Ile Arg Tyr Ser Ile Thr
        195                 200                 205
```

| | | | | | | | | | | | | | |
|---|---|---|---|---|---|---|---|---|---|---|---|---|---|
| Gly | Val 210 | Gly | Ala | Asp | Gln 215 | Pro | Met | Glu | Val 220 | Phe | Ser | Ile | Asn | Ser |
| Met 225 | Ser | Gly | Arg | Met 230 | Tyr | Val | Thr | Arg | Pro 235 | Met | Asp | Arg | Glu | Glu | His 240 |
| Ala | Ser | Tyr | His | Leu 245 | Arg | Ala | His | Ala | Val 250 | Asp | Met | Asn | Gly | Asn | Lys 255 |
| Val | Glu | Asn | Pro 260 | Ile | Asp | Leu | Tyr | Ile 265 | Tyr | Val | Ile | Asp | Met 270 | Asn | Asp |
| Asn | His | Pro 275 | Glu | Phe | Ile | Asn | Gln 280 | Val | Tyr | Asn | Cys | Ser 285 | Val | Asp | Glu |
| Gly | Ser | Lys | Pro 290 | Gly | Thr | Tyr | Val | Met 295 | Thr | Ile | Thr | Ala | Asn 300 | Asp | Ala |
| Asp 305 | Asp | Ser | Thr | Thr | Ala 310 | Asn | Gly | Met | Val | Arg 315 | Tyr | Arg | Ile | Val | Thr 320 |
| Gln | Thr | Pro | Gln | Ser 325 | Pro | Ser | Gln | Asn | Met 330 | Phe | Thr | Ile | Asn | Ser 335 | Glu |
| Thr | Gly | Asp | Ile 340 | Val | Thr | Val | Ala | Ala 345 | Gly | Trp | Asp | Arg | Glu 350 | Lys | Val |
| Gln | Gln | Tyr | Thr 355 | Val | Ile | Val | Gln 360 | Ala | Thr | Asp | Met | Glu 365 | Gly | Asn | Leu |
| Asn | Tyr 370 | Gly | Leu | Ser | Asn | Thr 375 | Ala | Thr | Ala | Ile | Ile 380 | Thr | Val | Thr | Asp |
| Val 385 | Asn | Asp | Asn | Pro | Ser 390 | Glu | Phe | Thr | Ala | Ser 395 | Thr | Phe | Ala | Gly | Glu 400 |
| Val | Pro | Glu | Asn | Ser 405 | Val | Glu | Thr | Val | Val 410 | Ala | Asn | Leu | Thr | Val 415 | Met |
| Asp | Arg | Asp | Gln 420 | Pro | His | Ser | Pro | Asn 425 | Trp | Asn | Ala | Val | Tyr 430 | Arg | Ile |
| Ile | Ser | Gly | Asp 435 | Pro | Ser | Gly | His 440 | Phe | Ser | Val | Arg | Thr 445 | Asp | Pro | Val |
| Thr | Asn | Glu 450 | Gly | Met | Val | Thr 455 | Val | Val | Lys | Ala | Val 460 | Asp | Tyr | Glu | Leu |
| Asn 465 | Arg | Ala | Phe | Met | Leu 470 | Thr | Val | Met | Val | Ser 475 | Asn | Gln | Ala | Pro | Leu 480 |
| Ala | Ser | Gly | Ile | Gln 485 | Met | Ser | Phe | Gln | Ser 490 | Thr | Ala | Gly | Val | Thr 495 | Ile |
| Ser | Ile | Met | Asp 500 | Ile | Asn | Glu | Ala | Pro 505 | Tyr | Phe | Pro | Ser | Asn 510 | His | Lys |
| Leu | Ile | Arg 515 | Leu | Glu | Glu | Gly | Val 520 | Pro | Pro | Gly | Thr | Val 525 | Leu | Thr | Thr |
| Phe | Ser 530 | Ala | Val | Asp | Pro | Asp 535 | Arg | Phe | Met | Gln | Gin 540 | Ala | Val | Arg | Tyr |
| Ser 545 | Lys | Leu | Ser | Asp | Pro 550 | Ala | Ser | Trp | Leu | His 555 | Ile | Asn | Ala | Thr | Asn 560 |
| Gly | Gln | Ile | Thr | Thr 565 | Val | Ala | Val | Leu | Asp 570 | Arg | Glu | Ser | Leu | Tyr 575 | Thr |
| Lys | Asn | Asn | Val 580 | Tyr | Glu | Ala | Thr | Phe 585 | Leu | Ala | Ala | Asp | Asn 590 | Gly | Ile |
| Pro | Pro | Ala 595 | Ser | Gly | Thr | Gly | Thr 600 | Leu | Gln | Ile | Tyr | Leu 605 | Ile | Asp | Ile |
| Asn | Asp | Asn 610 | Ala | Pro | Glu | Leu 615 | Leu | Pro | Lys | Glu | Ala 620 | Gln | Ile | Cys | Glu |
| Arg | Pro | Asn | Leu | Asn | Ala | Ile | Asn | Ile | Thr | Ala | Ala | Asp | Ala | Asp | Val |

|  625 |  |  | | 630 |  |  | | 635 |  |  | | 640 |
| --- | --- | --- | --- | --- | --- | --- | --- | --- | --- | --- | --- | --- |
| His | Pro | Asn | Ile | Gly | Pro | Tyr | Val | Phe | Leu | Pro | Phe | Val | Pro | Ala |
|  |  |  |  | 645 |  |  |  | 650 |  |  |  | 655 |

Ala Val Arg Lys Asn Trp Thr Ile Thr Arg Leu Asn Gly Asp Tyr Ala
            660                665                670

Gln Leu Ser Leu Arg Ile Leu Tyr Leu Glu Ala Gly Met Tyr Asp Val
            675                680                685

Pro Ile Ile Val Thr Asp Ser Gly Asn Pro Pro Leu Ser Asn Thr Ser
    690                695                700

Ile Ile Lys Val Lys Val Cys Pro Cys Asp Asp Asn Gly Asp Cys Thr
705             710                715                720

Thr Ile Gly Ala Val Ala Ala Ala Gly Leu Gly Thr Gly Ala Ile Val
                725                730                735

Ala Ile Leu Ile Cys Ile Leu Ile Leu Leu Thr Met Val Leu Leu Phe
            740                745                750

Val Met Trp Met Lys Arg Arg Glu Lys Glu Arg His Thr Lys Gln Leu
            755                760                765

Leu Ile Asp Pro Glu Asp Val Arg Glu Lys Ile Leu Lys Tyr Asp Asp
    770                775                780

Glu Glu Gly Gly Gly Glu Glu Asp Gln Asp Tyr Asp Leu Ser Gln Leu
785                 790                795                800

Gln Gln Pro Glu Ala Met Gly His Val Pro Ser Lys Ala Pro Gly Val
                805                810                815

Arg Arg Val Asp Glu Arg Pro Val Gly Pro Glu Pro Gln Tyr Pro Ile
            820                825                830

Arg Pro Met Val Pro His Pro Gly Asp Ile Gly Asp Phe Ile Asn Glu
            835                840                845

Gly Leu Arg Ala Ala Asp Asn Asp Pro Thr Ala Pro Pro Tyr Asp Ser
    850                855                860

Leu Leu Val Phe Asp Tyr Glu Gly Ser Gly Ser Thr Ala Gly Ser Val
865                 870                875                880

Ser Ser Leu Asn Ser Ser Ser Ser Gly Asp Gln Asp Tyr Asp Tyr Leu
            885                890                895

Asn Asp Trp Gly Pro Arg Phe Lys Lys Leu Ala Asp Met Tyr Gly Gly
            900                905                910

Gly Glu Glu Asp
        915

( 2 ) INFORMATION FOR SEQ ID NO:43:

( i ) SEQUENCE CHARACTERISTICS:
        ( A ) LENGTH: 3164 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
CTCCACTCAC  GCTCAGCCCT  GGACGGACAG  GCAGTCCAAC  GGAACAGAAA  CATCCCTCAG     60

CCCACAGGCA  CGATCTGTTC  CTCCTGGGAA  GATGCAGAGG  CTATGATGCT  CCTCGCCACA    120

TCGGGCGCCT  GCCTGGGCCT  GCTGGCAGTG  GCAGCAGTGG  CAGCAGCAGG  TGCTAACCCT    180

GCCCAACGGG  ACACCCACAG  CCTGCTGCCC  ACCCACCGGC  GCCAAAAGAG  AGATTGGATT    240

TGGAACCAGA  TGCACATTGA  TGAAGAGAAA  AACACCTCAC  TTCCCCATCA  TGTAGGCAAG    300

ATCAAGTCAA  GCGTGAGTCG  CAAGAATGCC  AAGTACCTGC  TCAAAGGAGA  ATATGTGGGC    360
```

```
AAGGTCTTCC GGGTCGATGC AGAGACAGGA GACGTGTTCG CCATTGAGAG GCTGGACCGG    420
GAGAATATCT CAGAGTACCA CCTCACTGCT GTCATTGTGG ACAAGGACAC TGGCGAAAAC    480
CTGGAGACTC CTTCCAGCTT CACCATCAAA GTTCATGACG TGAACGACAA CTGGCCTGTG    540
TTCACGCATC GGTTGTTCAA TGCGTCCGTG CCTGAGTCGT CGGCTGTGGG GACCTCAGTC    600
ATCTCTGTGA CAGCAGTGGA TGCAGACGAC CCCACTGTGG GAGACCACGC CTCTGTCATG    660
TACCAAATCC TGAAGGGGAA AGAGTATTTT GCCATCGATA ATTCTGGACG TATTATCACA    720
ATAACGAAAA GCTTGGACCG AGAGAAGCAG GCCAGGTATG AGATCGTGGT GGAAGCGCGA    780
GATGCCCAGG GCCTCCGGGG GGACTCGGGC ACGGCCACCG TGCTGGTCAC TCTGCAAGAC    840
ATCAATGACA ACTTCCCCTT CTTCACCCAG ACCAAGTACA CATTTGTCGT GCCTGAAGAC    900
ACCCGTGTGG GCACCTCTGT GGGCTCTCTG TTTGTTGAGG ACCCAGATGA GCCCCAGAAC    960
CGGATGACCA AGTACAGCAT CTTGCGGGGC GACTACCAGG ACGCTTTCAC CATTGAGACA   1020
AACCCCGCCC ACAACGAGGG CATCATCAAG CCCATGAAGC CTCTGGATTA TGAATACATC   1080
CAGCAATACA GCTTCATAGT CGAGGCCACA GACCCCACCA TCGACCTCCG ATACATGAGC   1140
CCTCCCGCGG GAAACAGAGC CCAGGTCATT ATCAACATCA CAGATGTGGA CGAGCCCCCC   1200
ATTTTCCAGC AGCCTTTCTA CCACTTCCAG CTGAAGGAAA ACCAGAAGAA GCCTCTGATT   1260
GGCACAGTGC TGGCCATGGA CCCTGATGCG GCTAGGCATA GCATTGGATA CTCCATCCGC   1320
AGGACCAGTG ACAAGGGCCA GTTCTTCCGA GTCACAAAAA AGGGGGACAT TTACAATGAG   1380
AAAGAACTGG ACAGAGAAGT CTACCCCTGG TATAACCTGA CTGTGGAGGC CAAAGAACTG   1440
GATTCCACTG GAACCCCCAC AGGAAAAGAA TCCATTGTGC AAGTCCACAT TGAAGTTTTG   1500
GATGAGAATG ACAATGCCCC GGAGTTTGCC AAGCCCTACC AGCCCAAAGT GTGTGAGAAC   1560
GCTGTCCATG CCAGCTGGT CCTGCAGATC TCCGCAATAG ACAAGGACAT AACACCACGA   1620
AACGTGAAGT TCAAATTCAT CTTGAATACT GAGAACAACT TTACCCTCAC GGATAATCAC   1680
GATAACACGG CCAACATCAC AGTCAAGTAT GGGCAGTTTG ACCGGGAGCA TACCAAGGTC   1740
CACTTCCTAC CCGTGGTCAT CTCAGACAAT GGGATGCCAA GTCGCACGGG CACCAGCACG   1800
CTGACCGTGG CCGTGTGCAA GTGCAACGAG CAGGGCGAGT TCACCTTCTG CGAGGATATG   1860
GCCGCCCAGG TGGGCGTGAG CATCCAGGCA GTGGTAGCCA TCTTACTCTG CATCCTCACC   1920
ATCACAGTGA TCACCCTGCT CATCTTCCTG CGGCGGCGGC TCCGGAAGCA GGCCCGCGCG   1980
CACGGCAAGA GCGTGCCGGA GATCCACGAG CAGCTGGTCA CCTACGACGA GGAGGGCGGC   2040
GGCGAGATGG ACACCACCAG CTACGATGTG TCGGTGCTCA ACTCGGTGCG CCGCGGCGGG   2100
GCCAAGCCCC CGCGGCCCGC GCTGGACGCC CGGCCTTCCC TCTATGCGCA GGTGCAGAAG   2160
CCACCGAGGC ACGCGCCTGG GGCACACGGA GGGCCCGGGG AGATGGCAGC CATGATCGAG   2220
GTGAAGAAGG ACGAGGCGGA CCACGACGGC GACGGCCCCC CCTACGACAC GCTGCACATC   2280
TACGGCTACG AGGGCTCCGA GTCCATAGCC GAGTCCCTCA GCTCCCTGGG CACCGACTCA   2340
TCCGACTCTG ACGTGGATTA CGACTTCCTT AACGACTGGG GACCCAGGTT AAGATGCTG   2400
GCTGAGCTGT ACGGCTCGGA CCCCCGGGAG GAGCTGCTGT ATTAGGCGGC CGAGGTCACT   2460
CTGGGCCTGG GGACCCAAAC CCCCTGCAGC CAGGCCAGT CAGACTCCAG GCACCACAGC   2520
CTCCAAAAAT GGCAGTGACT CCCCAGCCCA GCACCCCTTC CTCGTGGGTC CAGAGACCT   2580
CATCAGCCTT GGGATAGCAA ACTCCAGGTT CCTGAAATAT CCAGGAATAT ATGTCAGTGA   2640
TGACTATTCT CAAATGCTGG CAAATCCAGG CTGGTGTTCT GTCTGGGCTC AGACATCCAC   2700
ATAACCCTGT CACCCACAGA CCGCCGTCTA ACTCAAAGAC TTCCTCTGGC TCCCCAAGGC   2760
```

```
TGCAAAGCAA AACAGACTGT GTTAACTGC  TGCAGGGTCT TTTTCTAGGG TCCCTGAACG    2820

CCCTGGTAAG GCTGGTGAGG TCCTGGTGCC TATCTGCCTG GAGGCAAAGG CCTGGACAGC    2880

TTGACTTGTG GGGCAGGATT CTCTGCAGCC CATTCCCAAG GGAGACTGAC CATCATGCCC    2940

TCTCTCGGGA GCCCTAGCCC TGCTCCAACT CCATACTCCA CTCCAAGTGC CCCACCACTC    3000

CCCAACCCCT CTCCAGGCCT GTCAAGAGGG AGGAAGGGGC CCCATGGCAG CTCCTGACCT    3060

TGGGTCCTGA AGTGACCTCA CTGGCCTGCC ATGCCAGTAA CTGTGCTGTA CTGAGCACTG    3120

AACCACATTC AGGGAAATGG CTTATTAAAC TTTGAAGCAA CTGT                     3164
```

(2) INFORMATION FOR SEQ ID NO:44:

(i) SEQUENCE CHARACTERISTICS:
    (A) LENGTH: 780 amino acids
    (B) TYPE: amino acid
    (D) TOPOLOGY: linear (ii) MOLECULE TYPE: protein (xi) SEQUENCE DESCRIPTION: SEQ ID NO:44:

```
Met Met Leu Leu Ala Thr Ser Gly Ala Cys Leu Gly Leu Leu Ala Val
 1               5                  10                  15

Ala Ala Val Ala Ala Ala Gly Ala Asn Pro Ala Gln Arg Asp Thr His
             20                  25                  30

Ser Leu Leu Pro Thr His Arg Arg Gln Lys Arg Asp Trp Ile Trp Asn
         35                  40                  45

Gln Met His Ile Asp Glu Glu Lys Asn Thr Ser Leu Pro His His Val
     50                  55                  60

Gly Lys Ile Lys Ser Ser Val Ser Arg Lys Asn Ala Lys Tyr Leu Leu
 65                  70                  75                  80

Lys Gly Glu Tyr Val Gly Lys Val Phe Arg Val Asp Ala Glu Thr Gly
                 85                  90                  95

Asp Val Phe Ala Ile Glu Arg Leu Asp Arg Glu Asn Ile Ser Glu Tyr
             100                 105                 110

His Leu Thr Ala Val Ile Val Asp Lys Asp Thr Gly Glu Asn Leu Glu
         115                 120                 125

Thr Pro Ser Ser Phe Thr Ile Lys Val His Asp Val Asn Asp Asn Trp
     130                 135                 140

Pro Val Phe Thr His Arg Leu Phe Asn Ala Ser Val Pro Glu Ser Ser
145                 150                 155                 160

Ala Val Gly Thr Ser Val Ile Ser Val Thr Ala Val Asp Ala Asp Asp
                 165                 170                 175

Pro Thr Val Gly Asp His Ala Ser Val Met Tyr Gln Ile Leu Lys Gly
             180                 185                 190

Lys Glu Tyr Phe Ala Ile Asp Asn Ser Gly Arg Ile Ile Thr Ile Thr
         195                 200                 205

Lys Ser Leu Asp Arg Glu Lys Gln Ala Arg Tyr Glu Ile Val Val Glu
     210                 215                 220

Ala Arg Asp Ala Gln Gly Leu Arg Gly Asp Ser Gly Thr Ala Thr Val
225                 230                 235                 240

Leu Val Thr Leu Gln Asp Ile Asn Asp Asn Phe Pro Phe Phe Thr Gln
                 245                 250                 255

Thr Lys Tyr Thr Phe Val Val Pro Glu Asp Thr Arg Val Gly Thr Ser
             260                 265                 270

Val Gly Ser Leu Phe Val Glu Asp Pro Asp Glu Pro Gln Asn Arg Met
         275                 280                 285
```

```
Thr  Lys  Tyr  Ser  Ile  Leu  Arg  Gly  Asp  Tyr  Gln  Asp  Ala  Phe  Thr  Ile
     290                 295                 300

Glu  Thr  Asn  Pro  Ala  His  Asn  Glu  Gly  Ile  Ile  Lys  Pro  Met  Lys  Pro
305                      310                 315                           320

Leu  Asp  Tyr  Glu  Tyr  Ile  Gln  Gln  Tyr  Ser  Phe  Ile  Val  Glu  Ala  Thr
                    325                 330                           335

Asp  Pro  Thr  Ile  Asp  Leu  Arg  Tyr  Met  Ser  Pro  Pro  Ala  Gly  Asn  Arg
               340                 345                      350

Ala  Gln  Val  Ile  Ile  Asn  Ile  Thr  Asp  Val  Asp  Glu  Pro  Pro  Ile  Phe
          355                 360                      365

Gln  Gln  Pro  Phe  Tyr  His  Phe  Gln  Leu  Lys  Glu  Asn  Gln  Lys  Lys  Pro
370                      375                      380

Leu  Ile  Gly  Thr  Val  Leu  Ala  Met  Asp  Pro  Asp  Ala  Ala  Arg  His  Ser
385                      390                 395                           400

Ile  Gly  Tyr  Ser  Ile  Arg  Arg  Thr  Ser  Asp  Lys  Gly  Gln  Phe  Phe  Arg
                    405                 410                           415

Val  Thr  Lys  Lys  Gly  Asp  Ile  Tyr  Asn  Glu  Lys  Glu  Leu  Asp  Arg  Glu
               420                 425                      430

Val  Tyr  Pro  Trp  Tyr  Asn  Leu  Thr  Val  Glu  Ala  Lys  Glu  Leu  Asp  Ser
          435                 440                      445

Thr  Gly  Thr  Pro  Thr  Gly  Lys  Glu  Ser  Ile  Val  Gln  Val  His  Ile  Glu
     450                 455                 460

Val  Leu  Asp  Glu  Asn  Asp  Asn  Ala  Pro  Glu  Phe  Ala  Lys  Pro  Tyr  Gln
465                      470                 475                           480

Pro  Lys  Val  Cys  Glu  Asn  Ala  Val  His  Gly  Gln  Leu  Val  Leu  Gln  Ile
               485                 490                           495

Ser  Ala  Ile  Asp  Lys  Asp  Ile  Thr  Pro  Arg  Asn  Val  Lys  Phe  Lys  Phe
               500                 505                      510

Ile  Leu  Asn  Thr  Glu  Asn  Asn  Phe  Thr  Leu  Thr  Asp  Asn  His  Asp  Asn
          515                 520                      525

Thr  Ala  Asn  Ile  Thr  Val  Lys  Tyr  Gly  Gln  Phe  Asp  Arg  Glu  His  Thr
     530                 535                      540

Lys  Val  His  Phe  Leu  Pro  Val  Val  Ile  Ser  Asp  Asn  Gly  Met  Pro  Ser
545                      550                 555                           560

Arg  Thr  Gly  Thr  Ser  Thr  Leu  Thr  Val  Ala  Val  Cys  Lys  Cys  Asn  Glu
               565                 570                      575

Gln  Gly  Glu  Phe  Thr  Phe  Cys  Glu  Asp  Met  Ala  Ala  Gln  Val  Gly  Val
               580                 585                      590

Ser  Ile  Gln  Ala  Val  Val  Ala  Ile  Leu  Leu  Cys  Ile  Leu  Thr  Ile  Thr
          595                 600                      605

Val  Ile  Thr  Leu  Leu  Ile  Phe  Leu  Arg  Arg  Arg  Leu  Arg  Leu  Gln  Ala
     610                 615                      620

Arg  Ala  His  Gly  Lys  Ser  Val  Pro  Glu  Ile  His  Glu  Gln  Leu  Val  Thr
625                      630                 635                           640

Tyr  Asp  Glu  Glu  Gly  Gly  Gly  Glu  Met  Asp  Thr  Thr  Ser  Tyr  Asp  Val
               645                 650                      655

Ser  Val  Leu  Asn  Ser  Val  Arg  Arg  Gly  Gly  Ala  Lys  Pro  Pro  Arg  Pro
          660                 665                      670

Ala  Leu  Asp  Ala  Arg  Pro  Ser  Leu  Tyr  Ala  Gln  Val  Gln  Lys  Pro  Pro
          675                 680                      685

Arg  His  Ala  Pro  Gly  Ala  His  Gly  Gly  Pro  Gly  Glu  Met  Ala  Ala  Met
     690                 695                      700

Ile  Glu  Val  Lys  Lys  Asp  Glu  Ala  Asp  His  Asp  Gly  Asp  Gly  Pro  Pro
```

|  705 | | | | | 710 | | | | | 715 | | | | 720 |

Tyr Asp Thr Leu His Ile Tyr Gly Tyr Glu Gly Ser Glu Ser Ile Ala
            725                 730                 735

Glu Ser Leu Ser Ser Leu Gly Thr Asp Ser Ser Asp Ser Asp Val Asp
            740                 745                 750

Tyr Asp Phe Leu Asn Asp Trp Gly Pro Arg Phe Lys Met Leu Ala Glu
            755                 760                 765

Leu Tyr Gly Ser Asp Pro Arg Glu Glu Leu Leu Tyr
770                 775                 780

( 2 ) INFORMATION FOR SEQ ID NO:45:

( i ) SEQUENCE CHARACTERISTICS:
        ( A ) LENGTH: 1369 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

| | | | | | |
|---|---|---|---|---|---|
| TGTAGATGAG | CCACCTGTCT | TCAGCAAACT | GGCCTACATC | TTACAAATAA | GAGAAGATGC | 60 |
| TCAGATAAAC | ACCACAATAG | GCTCCGTCAC | AGCCCAAGAT | CCAGATGCTG | CCAGGAATCC | 120 |
| TGTCAAGTAC | TCTATAGATC | GACACACAGA | TATGGACAGA | ATATTCAACA | TTGATTCTGG | 180 |
| AAATGGTTCG | ATTTTACAT | CGAAACTTCT | TGACCGAGAA | ACACTGCTAT | GGCACAACAT | 240 |
| TACAGTGATA | GCAACAGAGA | TCAATAATCC | AAAGCAAAGT | AGTCGAGTAC | CTCTATATAT | 300 |
| TAAAGTTCTA | GATGTCAATG | ACAACGCCCC | AGAATTTGCT | GAGTTCTATG | AAACTTTTGT | 360 |
| CTGTGAAAAA | GCAAAGGCAG | ATCAGTTGAT | TCAGACCTTG | CATGCTGTTA | GCAAGGATGA | 420 |
| CCCTTATAGT | GGGCACCAAT | TTTCGTTTTC | CTTGGCCCCT | GAAGCAGCCA | GTGGCTCAAA | 480 |
| CTTTACCATT | CAAGACAACA | AAGACAACAC | GGCGGGAATC | TTAACTCGGA | AAAATGGCTA | 540 |
| TAATAGACAC | GAGATGAGCA | CCTATCTCTT | GCCTGTGGTC | ATTTCAGACA | ACGACTACCC | 600 |
| AGTTCAAAGC | AGCACTGGGA | CAGTGACTGT | CCGGGTCTGT | GCATGTGACC | ACCACGGGAA | 660 |
| CATGCAATCC | TGCCATGCGG | AGGCGCTCAT | CCACCCCACG | GGACTGAGCA | CGGGGGCTCT | 720 |
| GGTTGCCATC | CTTCTGTGCA | TCGTGATCCT | ACTAGTGACA | GTGGTGCTGT | TTGCAGCTCT | 780 |
| GAGGCGGCAG | CGAAAAAAAG | AGCCTTTGAT | CATTTCCAAA | GAGGACATCA | GAGATAACAT | 840 |
| TGTCAGTTAC | AACGACGAAG | GTGGTGGAGA | GGAGGACACC | CAGGCTTTTG | ATATCGGCAC | 900 |
| CCTGAGGAAT | CCTGAAGCCA | TAGAGGACAA | CAAATTACGA | AGGGACATTG | TGCCCGAAGC | 960 |
| CCTTTTCCTA | CCCCGACGGA | CTCCAACAGC | TCGCGACAAC | ACCGATGTCA | GAGATTTCAT | 1020 |
| TAACCAAAGG | TTAAAGGAAA | ATGACACGGA | CCCCACTGCC | CCGCCATACG | ACTCCCTGGC | 1080 |
| CACTTACGCC | TATGAAGGCA | CTGGCTCCGT | GGCGGATTCC | CTGAGCTCGC | TGGAGTCAGT | 1140 |
| GACCACGGAT | GCAGATCAAG | ACTATGATTA | CCTTTAGTGA | CTGGGACCTC | GATTCAAAAA | 1200 |
| GCTTGCAGAT | ATGTATGGAG | GAGTGGACAG | TGACAAAGAC | TCCTAATCTG | TTGCCTTTTT | 1260 |
| CATTTTCCAA | TACGACACTG | AAATATGTGA | AGTGGCTATT | TCTTTATATT | TATCCACTAC | 1320 |
| TCCGTGAAGG | CTTCTCTGTT | CTACCCGTTC | CAAAAGCCAA | TGGCTGCAG | | 1369 |

( 2 ) INFORMATION FOR SEQ ID NO:46:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Val  Asp  Glu  Pro  Pro  Val  Phe  Ser  Lys  Leu  Ala  Tyr  Ile  Leu  Gln  Ile
1                 5                      10                           15

Arg  Glu  Asp  Ala  Gln  Ile  Asn  Thr  Thr  Ile  Gly  Ser  Val  Thr  Ala  Gln
                 20                  25                           30

Asp  Pro  Asp  Ala  Ala  Arg  Asn  Pro  Val  Lys  Tyr  Ser  Ile  Lys  Arg  His
            35                       40                      45

Thr  Asp  Met  Asp  Arg  Ile  Phe  Asn  Ile  Asp  Ser  Gly  Asn  Gly  Ser  Ile
       50                     55                          60

Phe  Thr  Ser  Lys  Leu  Leu  Lys  Arg  Glu  Thr  Leu  Leu  Trp  His  Asn  Ile
65                      70                     75                            80

Thr  Val  Ile  Ala  Thr  Glu  Ile  Asn  Asn  Pro  Lys  Gln  Ser  Ser  Arg  Val
                      85                      90                         95

Pro  Leu  Tyr  Ile  Lys  Val  Leu  Asp  Val  Asn  Asp  Asn  Ala  Pro  Glu  Phe
                 100                     105                       110

Ala  Glu  Phe  Tyr  Glu  Thr  Phe  Val  Cys  Glu  Lys  Ala  Lys  Ala  Asp  Gln
            115                      120                      125

Leu  Ile  Gln  Thr  Leu  His  Ala  Val  Asp  Lys  Asp  Pro  Tyr  Ser  Gly
       130                     135                       140

His  Gln  Phe  Ser  Phe  Ser  Leu  Ala  Pro  Glu  Ala  Ala  Ser  Gly  Ser  Asn
145                     150                      155                          160

Phe  Thr  Ile  Gln  Asp  Asn  Lys  Asp  Asn  Thr  Ala  Gly  Ile  Leu  Thr  Arg
                    165                      170                       175

Lys  Asn  Gly  Tyr  Asn  Arg  His  Glu  Met  Ser  Thr  Tyr  Leu  Leu  Pro  Val
                 180                     185                       190

Val  Ile  Ser  Asp  Asn  Asp  Tyr  Pro  Val  Gln  Ser  Ser  Thr  Gly  Thr  Val
            195                      200                      205

Thr  Val  Arg  Val  Cys  Ala  Cys  Asp  His  His  Gly  Asn  Met  Gln  Ser  Cys
       210                     215                      220

His  Ala  Glu  Ala  Leu  Ile  His  Pro  Thr  Gly  Leu  Ser  Thr  Gly  Ala  Leu
225                     230                      235                          240

Val  Ala  Ile  Leu  Leu  Cys  Ile  Val  Ile  Leu  Leu  Val  Thr  Val  Val  Leu
                    245                      250                      255

Phe  Ala  Ala  Leu  Arg  Arg  Gln  Arg  Lys  Lys  Glu  Pro  Leu  Ile  Ile  Ser
                 260                     265                       270

Lys  Glu  Asp  Ile  Arg  Asp  Asn  Ile  Val  Ser  Tyr  Asn  Asp  Glu  Gly  Gly
            275                      280                      285

Gly  Glu  Glu  Asp  Thr  Gln  Ala  Phe  Asp  Ile  Gly  Thr  Leu  Arg  Asn  Pro
     290                      295                      300

Glu  Ala  Ile  Glu  Asp  Asn  Lys  Leu  Arg  Arg  Asp  Ile  Val  Pro  Glu  Ala
305                      310                      315                         320

Leu  Phe  Leu  Pro  Arg  Arg  Thr  Pro  Thr  Ala  Arg  Asp  Asn  Thr  Asp  Val
                    325                      330                      335

Arg  Asp  Phe  Ile  Asn  Gln  Arg  Leu  Lys  Glu  Asn  Asp  Thr  Asp  Pro  Thr
                 340                      345                      350

Ala  Pro  Pro  Tyr  Asp  Ser  Leu  Ala  Thr  Tyr  Ala  Tyr  Glu  Gly  Thr  Gly
            355                      360                      365

Ser  Val  Ala  Asp  Ser  Leu  Ser  Ser  Leu  Glu  Ser  Val  Thr  Thr  Asp  Ala
     370                      375                      380

Asp  Gln  Asp  Tyr  Asp  Tyr  Leu  Ser  Asp  Trp  Gly  Pro  Arg  Phe  Lys  Lys
385                      390                      395                         400
```

```
        Leu Ala Asp Met Tyr Gly Gly Val Asp Ser Asp Lys Asp Ser
                        405                 410
```

( 2 ) INFORMATION FOR SEQ ID NO:47:

( i ) SEQUENCE CHARACTERISTICS:
        ( A ) LENGTH: 2550 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

```
CAGGAAATGC TCTTGGATCT CTGGACTCCA TTAATAATAT TATGGATTAC TCTTCCCCCT      60
TGCATTTACA TGGCTCCGAT GAATCAGTCT CAAGTTTTAA TGAGTGGATC CCCTTTGGAA     120
CTAAACAGTC TGGGTGAAGA ACAGCGAATT TTGAACCGCT CCAAAAGAGG CTGGGTTTGG     180
AATCAAATGT TTGTCCTGGA AGAGTTTTCT GGACCTGAAC CGATTCTTGT TGGCCGGCTA     240
CACACAGACC TGGATCCTGG GAGCAAAAAA ATCAAGTATA TCCTATCAGG TGATGGAGCT     300
GGGACCATAT TTCAAATAAA TGATGTAACT GGAGATATCC ATGCTATAAA AAGACTTGAC     360
CGGGAGGAAA AGGCTGAGTA TACCCTAACA GCTCAAGCAG TGGACTGGGA GACAAGCAAA     420
CCTCTGGAGC CTCCTTCTGA ATTTATTATT AAAGTTCAAG ACATCAATGA CAATGCACCA     480
GAGTTTCTTA ATGGACCCTA TCATGCTACT GTGCCAGAAA TGTCCATTTT GGGTACATCT     540
GTCACTAACG TCACTGCGAC CGACGCTGAT GACCCAGTTT ATGGAAACAG TGCAAAGTTG     600
GTTTATAGTA TATTGGAAGG GCAGCCTTAT TTTTCCATTG AGCCTGAAAC AGCTATTATA     660
AAAACTGCCC TTCCCAACAT GGACAGAGAA GCCAAGGAGG AGTACCTGGT TGTTATCCAA     720
GCCAAAGATA TGGGTGGACA CTCTGGTGGC CTGTCTGGGA CCACGACACT TACAGTGACT     780
CTTACTGATG TTAATGACAA TCCTCCAAAA TTTGCACAGA GCCTGTATCA CTTCTCAGTA     840
CCGGAAGATG TGGTTCTTGG CACTGCAATA GGAAGGGTGA AGGCCAATGA TCAGGATATT     900
GGTGAAAATG CACAGTCATC ATATGATATC ATCGATGGAG ATGGAACAGC ACTTTTTGAA     960
ATCACTTCTG ATGCCCAGGC CCAGGATGGC ATTATAAGGC TAAGAAAACC TCTGGACTTT    1020
GAGACCAAAA AATCCTATAC GCTAAAGGAT GAGGCAGCCA ATGTCCATAT TGACCCACGC    1080
TTCAGTGGCA GGGGCCCTT TAAAGACACG GCGACAGTCA AATCGTGGT TGAAGATGCT    1140
GATGAGCCTC CGGTCTTCTC TTCACCGACT TACCTACTTG AAGTTCATGA AATGCTGCT    1200
CTAAACTCCG TGATTGGGCA AGTGACTGCT CGTGACCCTG ATATCACTTC CAGTCCTATA    1260
AGGTTTTCCA TCGACCGGCA CACTGACCTG GAGAGGCAGT TCAACATTAA TGCAGACGAT    1320
GGGAAGATAA CGCTGGCAAC ACCACTTGAC AGAGAATTAA GTGTATGGCA CAACATAACA    1380
ATCATTGCTA CTGAAATTAG GAACCACAGT CAGATATCAC GAGTACCTGT TGCTATTAAA    1440
GTGCTGGATG TCAATGACAA CGCCCCTGAA TTCGCATCCG AATATGAGGC ATTTTTATGT    1500
GAAAATGGAA AACCCGGCCA AGTCATTCAA ACTGTTAGCG CCATGGACAA AGATGATCCC    1560
AAAAACGGAC ATTATTTCTT ATACAGTCTC CTTCCAGAAA TGGTCAACAA TCCGAATTTC    1620
ACCATCAAGA AAAATGAAGA TAATTCCCTC AGTATTTTGG CAAAGCATAA TGGATTCAAC    1680
CGCCAGAAGC AAGAAGTCTA TCTTTTACCA ATCATAATCA GTGATAGTGG AAATCCTCCA    1740
CTGAGCAGCA CTAGCACCTT GACAATCAGG GTCTGTGGCT GCAGCAATGA CGGTGTCGTC    1800
CAGTCTTGCA ATGTCGAAGC TTATGTCCTT CCAATTGGAC TCAGTATGGG CGCCTTAATT    1860
GCCATATTAG CATGCATCAT TTTGCTGTTA GTCATCGTGG TGCTGTTTGT AACTCTACGG    1920
```

-continued

```
CGGCATCAAA AAAATGAACC ATTAATTATC AAAGATGATG AAGACGTTCG AGAAAACATC      1980

ATTCGCTACG ATGATGAAGG AGGAGGGGAG GAGGACACAG AGGCTTTTGA CATTGCAACT      2040

TTACAAAATC CAGATGGAAT TAATGGATTT TTACCCCGTA AGGATATTAA ACCAGATTTG      2100

CAGTTTATGC CAAGGCAAGG GCTTGCTCCA GTTCCAAATG GTGTTGATGT CGATGAATTT      2160

ATAAATGTAA GGCTGCATGA GGCAGATAAT GATCCCACAG CCCCGCCATA TGACTCCATT      2220

CAAATATATG GCTATGAAGG CCGAGGGTCA GTGGCTGGCT CCCTCAGCTC CTTGGAGTCC      2280

ACCACATCAG ACTCAGACCA GAATTTTGAC TACCTCAGTG ACTGGGGTCC CCGCTTTAAG      2340

AGACTGGGCG AACTCTACTC TGTTGGTGAA AGTGACAAAG AAACTTGACA GTGGATTATA      2400

AATAAATCAC TGGAACTGAG CATTCTGTAA TATTCTAGGG TCACTCCCCT TAGATACAAC      2460

CAATGTGGCT ATTTGTTTAG AGGCAAGTTT AGCACCAGTC ATCTATAACT CAACCACATT      2520

TAATGTTGAC AAAAAGATAA TAAATAAAAA                                       2550
```

( 2 ) INFORMATION FOR SEQ ID NO:48:

( i ) SEQUENCE CHARACTERISTICS:
        ( A ) LENGTH: 793 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Met Leu Leu Asp Leu Trp Thr Pro Leu Ile Ile Leu Trp Ile Thr Leu
  1               5                  10                  15

Pro Pro Cys Ile Tyr Met Ala Pro Met Asn Gln Ser Gln Val Leu Met
                 20                  25                  30

Ser Gly Ser Pro Leu Gln Leu Asn Ser Leu Gly Glu Glu Gln Arg Ile
             35                  40                  45

Leu Asn Arg Ser Lys Arg Gly Trp Val Trp Asn Gln Met Phe Val Leu
         50                  55                  60

Glu Glu Phe Ser Gly Pro Glu Pro Ile Leu Val Gly Arg Leu His Thr
 65                  70                  75                  80

Asp Leu Asp Pro Gly Ser Lys Lys Ile Lys Tyr Ile Leu Ser Gly Asp
                 85                  90                  95

Gly Ala Gly Thr Ile Phe Gln Ile Asn Asp Val Thr Gly Asp Ile His
                100                 105                 110

Ala Ile Lys Arg Leu Asp Arg Glu Glu Lys Ala Glu Tyr Thr Leu Thr
            115                 120                 125

Ala Gln Ala Val Asp Trp Glu Thr Ser Lys Pro Leu Glu Pro Pro Ser
        130                 135                 140

Glu Phe Ile Ile Lys Val Gln Asp Ile Asn Asp Asn Ala Pro Glu Phe
145                 150                 155                 160

Leu Asn Gly Pro Tyr His Ala Thr Val Pro Glu Met Ser Ile Leu Gly
                165                 170                 175

Thr Ser Val Thr Asn Val Thr Ala Thr Asp Ala Asp Asp Pro Val Tyr
            180                 185                 190

Gly Asn Ser Ala Lys Leu Val Tyr Ser Ile Leu Glu Gly Gln Pro Tyr
        195                 200                 205

Phe Ser Ile Glu Pro Glu Thr Ala Ile Ile Lys Thr Ala Leu Pro Asn
    210                 215                 220

Met Asp Arg Glu Ala Lys Glu Glu Tyr Leu Val Val Ile Gln Ala Lys
225                 230                 235                 240

Asp Met Gly Gly His Ser Gly Gly Leu Ser Gly Thr Thr Thr Leu Thr
```

```
                         245                        250                        255
Val  Thr  Leu  Thr  Asp  Val  Asn  Asp  Asn  Pro  Pro  Lys  Phe  Ala  Gln  Ser
               260                      265                      270

Leu  Tyr  His  Phe  Ser  Val  Pro  Glu  Asp  Val  Val  Leu  Gly  Thr  Ala  Ile
               275                      280                      285

Gly  Arg  Val  Lys  Ala  Asn  Asp  Gln  Asp  Ile  Gly  Glu  Asn  Ala  Gln  Ser
     290                      295                      300

Ser  Tyr  Asp  Ile  Ile  Asp  Gly  Asp  Gly  Thr  Ala  Leu  Phe  Glu  Ile  Thr
305                           310                      315                      320

Ser  Asp  Ala  Gln  Ala  Gln  Asp  Gly  Ile  Ile  Arg  Leu  Arg  Lys  Pro  Leu
                ようし325                      330                      335

Asp  Phe  Glu  Thr  Lys  Lys  Ser  Tyr  Thr  Leu  Lys  Asp  Glu  Ala  Ala  Asn
               340                      345                      350

Val  His  Ile  Asp  Pro  Arg  Phe  Ser  Gly  Arg  Gly  Pro  Phe  Lys  Asp  Thr
               355                      360                      365

Ala  Thr  Val  Lys  Ile  Val  Glu  Asp  Ala  Asp  Glu  Pro  Pro  Val  Phe
               370                      375                      380

Ser  Ser  Pro  Thr  Tyr  Leu  Leu  Glu  Val  His  Glu  Asn  Ala  Ala  Leu  Asn
385                           390                      395                      400

Ser  Val  Ile  Gly  Gln  Val  Thr  Ala  Arg  Asp  Pro  Asp  Ile  Thr  Ser  Ser
                    405                      410                      415

Pro  Ile  Arg  Phe  Ser  Ile  Asp  Arg  His  Thr  Asp  Leu  Glu  Arg  Gln  Phe
               420                      425                      430

Asn  Ile  Asn  Ala  Asp  Asp  Gly  Lys  Ile  Thr  Leu  Ala  Thr  Pro  Leu  Asp
               435                      440                      445

Arg  Glu  Leu  Ser  Val  Trp  His  Asn  Ile  Thr  Ile  Ala  Thr  Glu  Ile
450                           455                      460

Arg  Asn  His  Ser  Gln  Ile  Ser  Arg  Val  Pro  Val  Ala  Ile  Lys  Val  Leu
465                      470                      475                           480

Asp  Val  Asn  Asp  Asn  Ala  Pro  Glu  Phe  Ala  Ser  Glu  Tyr  Glu  Ala  Phe
               485                      490                      495

Leu  Cys  Glu  Asn  Gly  Lys  Pro  Gly  Gln  Val  Ile  Gln  Thr  Val  Ser  Ala
               500                      505                      510

Met  Asp  Lys  Asp  Asp  Pro  Lys  Asn  Gly  His  Tyr  Phe  Leu  Tyr  Ser  Leu
               515                      520                      525

Leu  Pro  Glu  Met  Val  Asn  Asn  Pro  Asn  Phe  Thr  Ile  Lys  Lys  Asn  Glu
     530                      535                      540

Asp  Asn  Ser  Leu  Ser  Ile  Leu  Ala  Lys  His  Asn  Gly  Phe  Asn  Arg  Gln
545                           550                      555                      560

Lys  Gln  Glu  Val  Tyr  Leu  Leu  Pro  Ile  Ile  Ile  Ser  Asp  Ser  Gly  Asn
                    565                      570                      575

Pro  Pro  Leu  Ser  Ser  Thr  Ser  Thr  Leu  Thr  Ile  Arg  Val  Cys  Gly  Cys
               580                      585                      590

Ser  Asn  Asp  Gly  Val  Val  Gln  Ser  Cys  Asn  Val  Glu  Ala  Tyr  Val  Leu
               595                      600                      605

Pro  Ile  Gly  Leu  Ser  Met  Gly  Ala  Leu  Ile  Ala  Ile  Leu  Ala  Cys  Ile
     610                      615                      620

Ile  Leu  Leu  Leu  Val  Ile  Val  Val  Leu  Phe  Val  Thr  Leu  Arg  Arg  His
625                      630                      635                           640

Gln  Lys  Asn  Glu  Pro  Leu  Ile  Ile  Lys  Asp  Asp  Glu  Asp  Val  Arg  Glu
               645                      650                      655

Asn  Ile  Ile  Arg  Tyr  Asp  Asp  Glu  Gly  Gly  Gly  Glu  Glu  Asp  Thr  Glu
               660                      665                      670
```

```
       Ala  Phe  Asp  Ile  Ala  Thr  Leu  Gln  Asn  Pro  Asp  Gly  Ile  Asn  Gly  Phe
            675                      680                      685

Leu  Pro  Arg  Lys  Asp  Ile  Lys  Pro  Asp  Leu  Gln  Phe  Met  Pro  Arg  Gln
            690                      695                      700

Gly  Leu  Ala  Pro  Val  Pro  Asn  Gly  Val  Asp  Val  Asp  Glu  Phe  Ile  Asn
       705                      710                      715                      720

Val  Arg  Leu  His  Glu  Ala  Asp  Asn  Asp  Pro  Thr  Ala  Pro  Pro  Tyr  Asp
                           725                      730                      735

Ser  Ile  Gln  Ile  Tyr  Gly  Tyr  Glu  Gly  Arg  Gly  Ser  Val  Ala  Gly  Ser
                      740                      745                      750

Leu  Ser  Ser  Leu  Glu  Ser  Thr  Thr  Ser  Asp  Ser  Asp  Gln  Asn  Phe  Asp
                 755                      760                      765

Tyr  Leu  Ser  Asp  Trp  Gly  Pro  Arg  Phe  Lys  Arg  Leu  Gly  Glu  Leu  Tyr
            770                      775                      780

Ser  Val  Gly  Glu  Ser  Asp  Lys  Glu  Thr
       785                      790
```

( 2 ) INFORMATION FOR SEQ ID NO:49:

( i ) SEQUENCE CHARACTERISTICS:
        ( A ) LENGTH: 730 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..730

( x i ) SEQUENCE DESCRIPTION: SEQ ID NO:49:

```
G  AAT  TCG  AGC  TCG  GTA  CCC  GGG  GAT  CCT  CTA  GAG  TCG  ACC  TGC  AGT         46
   Asn  Ser  Ser  Ser  Val  Pro  Gly  Asp  Pro  Leu  Glu  Ser  Thr  Cys  Ser
   1              5                        10                      15

GCT  GAA  GCC  CTG  CTC  CTC  CCT  GCC  GGC  CTC  AGC  ACT  GGG  GCC  TTG  ATC        94
Ala  Glu  Ala  Leu  Leu  Leu  Pro  Ala  Gly  Leu  Ser  Thr  Gly  Ala  Leu  Ile
                    20                       25                       30

GCC  ATC  CTC  CTC  TGC  ATC  ATC  ATT  CTA  CTG  GTT  ATA  GTA  GTA  CTG  TTT       142
Ala  Ile  Leu  Leu  Cys  Ile  Ile  Ile  Leu  Leu  Val  Ile  Val  Val  Leu  Phe
               35                       40                       45

GCA  GCT  CTG  AAA  AGA  CAG  CGA  AAA  AAA  GAG  CCT  CTG  ATC  TTG  TCA  AAA       190
Ala  Ala  Leu  Lys  Arg  Gln  Arg  Lys  Lys  Glu  Pro  Leu  Ile  Leu  Ser  Lys
          50                       55                       60

GAA  GAT  ATC  AGA  GAC  AAC  ATT  GTG  AGC  TAT  AAC  GAT  GAG  GGT  GGT  GGA       238
Glu  Asp  Ile  Arg  Asp  Asn  Ile  Val  Ser  Tyr  Asn  Asp  Glu  Gly  Gly  Gly
     65                       70                       75

GAG  GAG  GAC  ACC  CAG  GCC  TTT  GAT  ATC  GGC  ACC  CTG  AGG  AAT  CCT  GCA       286
Glu  Glu  Asp  Thr  Gln  Ala  Phe  Asp  Ile  Gly  Thr  Leu  Arg  Asn  Pro  Ala
80                       85                       90                       95

GCC  ATT  GAG  GAA  AAA  AAG  CTC  CGG  CGA  GAT  ATT  ATT  CCA  GAA  ACG  TTA       334
Ala  Ile  Glu  Glu  Lys  Lys  Leu  Arg  Arg  Asp  Ile  Ile  Pro  Glu  Thr  Leu
                    100                      105                      110

TTT  ATT  CCT  CGG  AGG  ACT  CCT  ACA  GCT  CCA  GAT  AAC  ACG  GAC  GTC  CGG       382
Phe  Ile  Pro  Arg  Arg  Thr  Pro  Thr  Ala  Pro  Asp  Asn  Thr  Asp  Val  Arg
               115                      120                      125

GAT  TTC  ATT  AAT  GAA  AGG  CTA  AAA  GAG  CAT  GAT  CTT  GAC  CCC  ACC  GCA       430
Asp  Phe  Ile  Asn  Glu  Arg  Leu  Lys  Glu  His  Asp  Leu  Asp  Pro  Thr  Ala
          130                      135                      140

CCC  CCC  TAC  GAC  TCA  CTT  GCA  ACC  TAT  GCC  TAT  GAA  GGA  AAT  GAT  TCC       478
Pro  Pro  Tyr  Asp  Ser  Leu  Ala  Thr  Tyr  Ala  Tyr  Glu  Gly  Asn  Asp  Ser
```

|     |     |     |     | 145 |     |     |     | 150 |     |     |     | 155 |     |     |     |
|-----|-----|-----|-----|-----|-----|-----|-----|-----|-----|-----|-----|-----|-----|-----|-----|
| ATT | GCT | GAA | TCT | CTG | AGT | TCA | TTA | GAA | TCA | GGT | ACT | ACT | GAA | GGA | GAC | 526 |
| Ile | Ala | Glu | Ser | Leu | Ser | Ser | Leu | Glu | Ser | Gly | Thr | Thr | Glu | Gly | Asp |
| 160 |     |     |     |     | 165 |     |     |     | 170 |     |     |     |     |     | 175 |

| CAA | AAC | TAC | GAT | TAC | CTC | CGA | GAA | TGG | GGC | CCT | CGG | TTT | AAT | AAG | CTA | 574 |
| Gln | Asn | Tyr | Asp | Tyr | Leu | Arg | Glu | Trp | Gly | Pro | Arg | Phe | Asn | Lys | Leu |
|     |     |     |     | 180 |     |     |     |     | 185 |     |     |     |     | 190 |     |

| GCA | GAA | ATG | TAT | GGT | GGT | GGG | GAA | AGT | GAC | AAA | GAC | TCT | TAA | CGT | AGG | 622 |
| Ala | Glu | Met | Tyr | Gly | Gly | Gly | Glu | Ser | Asp | Lys | Asp | Ser | *   | Arg | Arg |
|     |     |     | 195 |     |     |     |     | 200 |     |     |     |     | 205 |     |     |

| ATA | TAT | GTT | CTG | TTC | AAA | CAA | GAG | AAA | GTA | ACT | CTA | CCC | ATG | CTG | TCT | 670 |
| Ile | Tyr | Val | Leu | Phe | Lys | Gln | Glu | Lys | Val | Thr | Leu | Pro | Met | Leu | Ser |
|     |     | 210 |     |     |     |     | 215 |     |     |     |     | 220 |     |     |     |

| CCA | CTT | CAC | AAT | ATT | TGA | TAT | TCA | GGA | GCA | TTT | CCT | GCA | GTC | AGC | ACA | 718 |
| Pro | Leu | His | Asn | Ile | *   | Tyr | Ser | Gly | Ala | Phe | Pro | Ala | Val | Ser | Thr |
|     |     | 225 |     |     |     |     | 230 |     |     |     | 235 |     |     |     |     |

| ATT | TTT | TTC | TCA | | | | | | | | | | | | | 730 |
| Ile | Phe | Phe | Ser |
| 240 |

( 2 ) INFORMATION FOR SEQ ID NO:50:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| Asn | Ser | Ser | Ser | Val | Pro | Gly | Asp | Pro | Leu | Glu | Ser | Thr | Cys | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Ala | Leu | Leu | Leu | Pro | Ala | Gly | Leu | Ser | Thr | Gly | Ala | Leu | Ile | Ala |
|     |     |     |     | 20  |     |     |     |     | 25  |     |     |     |     | 30  |     |

| Ile | Leu | Leu | Cys | Ile | Ile | Ile | Leu | Leu | Val | Ile | Val | Val | Leu | Phe | Ala |
|     |     |     | 35  |     |     |     |     | 40  |     |     |     |     | 45  |     |     |

| Ala | Leu | Lys | Arg | Gln | Arg | Lys | Lys | Glu | Pro | Leu | Ile | Leu | Ser | Lys | Glu |
|     |     | 50  |     |     |     |     | 55  |     |     |     |     | 60  |     |     |     |

| Asp | Ile | Arg | Asp | Asn | Ile | Val | Ser | Tyr | Asn | Asp | Glu | Gly | Gly | Gly | Glu |
| 65  |     |     |     |     | 70  |     |     |     |     | 75  |     |     |     |     | 80  |

| Glu | Asp | Thr | Gln | Ala | Phe | Asp | Ile | Gly | Thr | Leu | Arg | Asn | Pro | Ala | Ala |
|     |     |     |     | 85  |     |     |     |     | 90  |     |     |     |     | 95  |     |

| Ile | Glu | Glu | Lys | Lys | Leu | Arg | Arg | Asp | Ile | Ile | Pro | Glu | Thr | Leu | Phe |
|     |     |     | 100 |     |     |     |     | 105 |     |     |     |     | 110 |     |     |

| Ile | Pro | Arg | Arg | Thr | Pro | Thr | Ala | Pro | Asp | Asn | Thr | Asp | Val | Arg | Asp |
|     |     |     | 115 |     |     |     |     | 120 |     |     |     |     | 125 |     |     |

| Phe | Ile | Asn | Glu | Arg | Leu | Lys | Glu | His | Asp | Leu | Asp | Pro | Thr | Ala | Pro |
|     | 130 |     |     |     |     | 135 |     |     |     |     | 140 |     |     |     |     |

| Pro | Tyr | Asp | Ser | Leu | Ala | Thr | Tyr | Ala | Tyr | Glu | Gly | Asn | Asp | Ser | Ile |
| 145 |     |     |     |     | 150 |     |     |     |     | 155 |     |     |     |     | 160 |

| Ala | Glu | Ser | Leu | Ser | Ser | Leu | Glu | Ser | Gly | Thr | Thr | Glu | Gly | Asp | Gln |
|     |     |     |     | 165 |     |     |     |     | 170 |     |     |     |     | 175 |     |

| Asn | Tyr | Asp | Tyr | Leu | Arg | Glu | Trp | Gly | Pro | Arg | Phe | Asn | Lys | Leu | Ala |
|     |     |     | 180 |     |     |     |     | 185 |     |     |     |     | 190 |     |     |

| Glu | Met | Tyr | Gly | Gly | Gly | Glu | Ser | Asp | Lys | Asp | Ser | Arg | Arg | Ile | Tyr |
|     |     | 195 |     |     |     |     | 200 |     |     |     |     | 205 |     |     |     |

| Val | Leu | Phe | Lys | Gln | Glu | Lys | Val | Thr | Leu | Pro | Met | Leu | Ser | Pro | Leu |
|     | 210 |     |     |     |     | 215 |     |     |     |     | 220 |     |     |     |     |

```
His Asn Ile Tyr Ser Gly Ala Phe Pro Ala Val Ser Thr Ile Phe Phe
225                 230                 235                 240

Ser
```

( 2 ) INFORMATION FOR SEQ ID NO:51:

( i ) SEQUENCE CHARACTERISTICS:
      ( A ) LENGTH: 2625 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:51:

| | | | | | |
|---|---|---|---|---|---|
| CGGCAGCCCT | GACGTGATGA | GCTCAACCAG | CAGAGACATT | CCATCCCAAG | AGAGGTCTGC | 60 |
| GTGACGCGTC | CGGGAGGCCA | CCCTCAGCAA | GACCACCGTA | CAGTTGGTGG | AAGGGGTGAC | 120 |
| AGCTGCATTC | TCCTGTGCCT | ACCACGTAAC | CAAAAATGAA | GGAGAACTAC | TGTTTACAAG | 180 |
| CCGCCCTGGT | GTGCCTGGGC | ATGCTGTGCC | ACAGCCATGC | CTTTGCCCCA | GAGCGGCGGG | 240 |
| GGCACCTGCG | GCCCTCCTTC | CATGGGCACC | ATGAGAAGGG | CAAGGAGGGG | CAGGTGCTAC | 300 |
| AGCGCTCCAA | GCGTGGCTGG | GTCTGGAACC | AGTTCTTCGT | GATAGAGGAG | TACACCGGGC | 360 |
| CTGACCCCGT | GCTTGTGGGC | AGGCTTCATT | CAGATATTGA | CTCTGGTGAT | GGGAACATTA | 420 |
| AATACATTCT | CTCAGGGGAA | GGAGCTGGAA | CCATTTTTGT | GATTGATGAC | AAATCAGGGA | 480 |
| ACATTCATGC | CACCAAGACG | TTGGATCGAG | AAGAGAGAGC | CCAGTACACG | TTGATGGCTC | 540 |
| AGGCGGTGGA | CAGGGACACC | AATCGGCCAC | TGGAGCCACC | GTCGGAATTC | ATTGTCAAGG | 600 |
| TCCAGGACAT | TAATGACAAC | CCTCCGGAGT | TCCTGCACGA | GACCTATCAT | GCCAACGTGC | 660 |
| CTGAGAGGTC | CAATGTGGGA | ACGTCAGTAA | TCCAGGTGAC | AGCTTCAGAT | GCAGATGACC | 720 |
| CCACTTATGG | AAATAGCGCC | AAGTTAGTGT | ACAGTATCCT | CGAAGGACAA | CCCTATTTTT | 780 |
| CGGTGGAAGC | ACAGACAGGT | ATCATCAGAA | CAGCCCTACC | CAACATGGAC | AGGGAGGCCA | 840 |
| AGGAGGAGTA | CCACGTGGTG | ATCCAGGCCA | AGGACATGGG | TGGACATATG | GGCGGACTCT | 900 |
| CAGGGACAAC | CAAAGTGACG | ATCACACTGA | CCGATGTCAA | TGACAACCCA | CCAAAGTTTC | 960 |
| CGCAGAGGCT | ATACCAGATG | TCTGTGTCAG | AAGCAGCCGT | CCCTGGGGAG | GAAGTAGGAA | 1020 |
| GAGTGAAAGC | TAAAGATCCA | GACATTGGAG | AAAATGGCTT | AGTCACATAC | AATATTGTTG | 1080 |
| ATGGAGATGG | TATGGAATCG | TTTGAAATCA | CAACGGACTA | TGAAACACAG | GAGGGGGTGA | 1140 |
| TAAAGCTGAA | AAAGCCTGTA | GATTTTGAAA | CCGAAAGAGC | CTATAGCTTG | AAGGTAGAGG | 1200 |
| CAGCCAACGT | GCACATCGAC | CCGAAGTTTA | TCAGCAATGG | CCCTTTCAAG | GACACTGTGA | 1260 |
| CCGTCAAGAT | CTCAGTAGAA | GATGCTGATG | AGCCCCCTAT | GTTCTTGGCC | CCAAGTTACA | 1320 |
| TCCACGAAGT | CCAAGAAAAT | GCAGCTGCTG | GCACCGTGGT | TGGGAGAGTG | CATGCCAAAG | 1380 |
| ACCCTGATGC | TGCCAACAGC | CCGATAAGGT | ATTCCATCGA | TCGTCACACT | GACCTCGACA | 1440 |
| GATTTTTCAC | TATTAATCCA | GAGGATGGTT | TTATTAAAAC | TACAAAACCT | CTGGATAGAG | 1500 |
| AGGAAACAGC | CTGGCTCAAC | ATCACTGTCT | TTGCAGCAGA | AATCCACAAT | CGGCATCAGG | 1560 |
| AAGCCCAAGT | CCCAGTGGCC | ATTAGGGTCC | TTGATGTCAA | CGATAATGCT | CCCAAGTTTG | 1620 |
| CTGCCCCTTA | TGAAGGTTTC | ATCTGTGAGA | GTGATCAGAC | CAAGCCACTT | TCCAACCAGC | 1680 |
| CAATTGTTAC | AATTAGTGCA | GATGACAAGG | ATGACACGGC | CAATGGACCA | AGATTTATCT | 1740 |
| TCAGCCTACC | CCCTGAAATC | ATTCACAATC | CAAATTTCAC | AGTCAGAGAC | AACCGAGATA | 1800 |
| ACACAGCAGG | CGTGTACGCC | CGGCGTGGAG | GGTTCAGTCG | GCAGAAGCAG | GACTTGTACC | 1860 |

```
TTCTGCCCAT AGTGATCAGC GATGGCGGCA TCCCGCCCAT GAGTAGCACC AACACCCTCA      1920

CCATCAAAGT CTGCGGGTGC GACGTGAACG GGGCACTGCT CTCCTGCAAC GCAGAGGCCT      1980

ACATTCTGAA CGCCGGCCTG AGCACAGGCG CCCTGATCGC CATCCTCGCC TGCATCGTCA      2040

TTCTCCTGGT CATTGTAGTA TTGTTTGTGA CCCTGAGAAG GCAAAAGAAA GAACCACTCA      2100

TTGTCTTTGA GGAAGAAGAT GTCCGTGAGA ACATCATTAC TTATGATGAT GAAGGGGGTG      2160

GGGAAGAAGA CACAGAAGCC TTTGATATTG CCACCCTCCA GAATCCTGAT GGTATCAATG      2220

GATTTATCCC CCGCAAAGAC ATCAAACCTG AGTATCAGTA CATGCCTAGA CCTGGGCTCC      2280

GGCCAGCGCC CAACAGCGTG GATGTCGATG ACTTCATCAA CACGAGAATA CAGGAGGCAG      2340

ACAATGACCC CACGGCTCCT CCTTATGACT CCATTCAAAT CTACGGTTAT GAAGGCAGGG      2400

GCTCAGTGGC CGGGTCCCTG AGCTCCCTAG AGTCGGCCAC CACAGATTCA GACTTGGACT      2460

ATGATTATCT ACAGAACTGG GGACCTCGTT TTAAGAAACT AGCAGATTTG TATGGTTCCA      2520

AAGACACTTT TGATGACGAT TCTTAACAAT AACGATACAA ATTTGGCCTT AAGAACTGTG      2580

TCTGGCGTTC TCAAGAATCT AGAAGATGTG TAACAGGTAT TTTTT                     2625
```

( 2 ) INFORMATION FOR SEQ ID NO:52:

( i ) SEQUENCE CHARACTERISTICS:
        ( A ) LENGTH: 796 amino acids
        ( B ) TYPE: amino acid
        ( D ) TOPOLOGY: linear ( i i ) MOLECULE TYPE: protein ( x i ) SEQUENCE DESCRIPTION: SEQ ID NO:52:

```
Met Lys Glu Asn Tyr Cys Leu Gln Ala Ala Leu Val Cys Leu Gly Met
 1               5                  10                  15

Leu Cys His Ser His Ala Phe Ala Pro Glu Arg Arg Gly His Leu Arg
             20                  25                  30

Pro Ser Phe His Gly His His Glu Lys Gly Lys Glu Gly Gln Val Leu
         35                  40                  45

Gln Arg Ser Lys Arg Gly Trp Val Trp Asn Gln Phe Phe Val Ile Glu
     50                  55                  60

Glu Tyr Thr Gly Pro Asp Pro Val Leu Val Gly Arg Leu His Ser Asp
 65                  70                  75                  80

Ile Asp Ser Gly Asp Gly Asn Ile Lys Tyr Ile Leu Ser Gly Glu Gly
                 85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
    130                 135                 140

Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Pro Thr Tyr Gly
            180                 185                 190

Asn Ser Ala Lys Leu Val Tyr Ser Ile Leu Glu Gly Gln Pro Tyr Phe
        195                 200                 205

Ser Val Glu Ala Gln Thr Gly Ile Ile Arg Thr Ala Leu Pro Asn Met
    210                 215                 220
```

```
Asp Arg Glu Ala Lys Glu Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255

Thr Leu Thr Asp Val Asn Asp Asn Pro Pro Lys Phe Pro Gln Arg Leu
            260                 265                 270

Tyr Gln Met Ser Val Ser Glu Ala Ala Val Pro Gly Glu Val Gly
        275                 280                 285

Arg Val Lys Ala Lys Asp Pro Asp Ile Gly Glu Asn Gly Leu Val Thr
    290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Lys Pro Val Asp
            325                 330                 335

Phe Glu Thr Glu Arg Ala Tyr Ser Leu Lys Val Glu Ala Ala Asn Val
            340                 345                 350

His Ile Asp Pro Lys Phe Ile Ser Asn Gly Pro Phe Lys Asp Thr Val
        355                 360                 365

Thr Val Lys Ile Ser Val Glu Asp Ala Asp Glu Pro Pro Met Phe Leu
    370                 375                 380

Ala Pro Ser Tyr Ile His Glu Val Gln Glu Asn Ala Ala Ala Gly Thr
385                 390                 395                 400

Val Val Gly Arg Val His Ala Lys Asp Pro Asp Ala Ala Asn Ser Pro
                405                 410                 415

Ile Arg Tyr Ser Ile Asp Arg His Thr Asp Leu Asp Arg Phe Phe Thr
            420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
    450                 455                 460

Asn Arg His Gln Glu Ala Gln Val Pro Val Ala Ile Arg Val Leu Asp
465                 470                 475                 480

Val Asn Asp Asn Ala Pro Lys Phe Ala Ala Pro Tyr Glu Gly Phe Ile
                485                 490                 495

Cys Glu Ser Asp Gln Thr Lys Pro Leu Ser Asn Gln Pro Ile Val Thr
            500                 505                 510

Ile Ser Ala Asp Asp Lys Asp Asp Thr Ala Asn Gly Pro Arg Phe Ile
            515                 520                 525

Phe Ser Leu Pro Pro Glu Ile Ile His Asn Pro Asn Phe Thr Val Arg
530                 535                 540

Asp Asn Arg Asp Asn Thr Ala Gly Val Tyr Ala Arg Arg Gly Gly Phe
545                 550                 555                 560

Ser Arg Gln Lys Gln Asp Leu Tyr Leu Leu Pro Ile Val Ile Ser Asp
            565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
        595                 600                 605

Tyr Ile Leu Asn Ala Gly Leu Ser Thr Gly Ala Leu Ile Ala Ile Leu
    610                 615                 620

Ala Cys Ile Val Ile Leu Leu Val Ile Val Val Leu Phe Val Thr Leu
625                 630                 635                 640

Arg Arg Gln Lys Lys Glu Pro Leu Ile Val Phe Glu Glu Glu Asp Val
            645                 650                 655
```

| | | | | | | | | | | | | | | |
|---|---|---|---|---|---|---|---|---|---|---|---|---|---|---|
|Arg|Glu|Asn|Ile|Ile|Thr|Tyr|Asp|Asp|Glu|Gly|Gly|Gly|Glu|Asp|
| | | |660| | | |665| | | |670| | | |
|Thr|Glu|Ala|Phe|Asp|Ile|Ala|Thr|Leu|Gln|Asn|Pro|Asp|Gly|Ile|Asn|
| | |675| | | |680| | | |685| | | | |
|Gly|Phe|Ile|Pro|Arg|Lys|Asp|Ile|Lys|Pro|Glu|Tyr|Gln|Tyr|Met|Pro|
| |690| | | |695| | | |700| | | | | |
|Arg|Pro|Gly|Leu|Arg|Pro|Ala|Pro|Asn|Ser|Val|Asp|Val|Asp|Asp|Phe|
|705| | | |710| | | |715| | | | | |720|
|Ile|Asn|Thr|Arg|Ile|Gln|Glu|Ala|Asp|Asn|Asp|Pro|Thr|Ala|Pro|Pro|
| | | |725| | | |730| | | |735| | | |
|Tyr|Asp|Ser|Ile|Gln|Ile|Tyr|Gly|Tyr|Glu|Gly|Arg|Gly|Ser|Val|Ala|
| | |740| | | |745| | | |750| | | | |
|Gly|Ser|Leu|Ser|Ser|Leu|Glu|Ser|Ala|Thr|Thr|Asp|Ser|Asp|Leu|Asp|
| |755| | | |760| | | |765| | | | | |
|Tyr|Asp|Tyr|Leu|Gln|Asn|Trp|Gly|Pro|Arg|Phe|Lys|Lys|Leu|Ala|Asp|
| |770| | | |775| | | |780| | | | | |
|Leu|Tyr|Gly|Ser|Lys|Asp|Thr|Phe|Asp|Asp|Asp|Ser|
|785| | | |790| | | |795| | | |

(2) INFORMATION FOR SEQ ID NO:53:

(i) SEQUENCE CHARACTERISTICS:
        (A) LENGTH: 2521 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

| | | | | | |
|---|---|---|---|---|---|
|CGGTGGAGGC|CACAGACACC|TCAAACCTGG|ATTCCACAAT|TCTACGTTAA|GTGTTGGAGT|60|
|TTTTATTACT|CTGCTGTAGG|AAAGCCTTTG|CCAATGCTTA|CAAGGAACTG|TTTATCCCTG|120|
|CTTCTCTGGG|TTCTGTTTGA|TGGAGGTCTC|CTAACACCAC|TACAACCACA|GCCACAGCAG|180|
|ACTTTAGCCA|CAGAGCCAAG|AGAAAATGTT|ATCCATCTGC|AGGACAACG|GTCACATTTC|240|
|CAACGTGTTA|AACGTGGCTG|GGTATGGAAT|CAATTTTTTG|TGCTGGAAGA|ATACGTGGGC|300|
|TCCGAGCCTC|AGTATGTGGG|AAAGCTCCAT|TCCGACTTAG|ACAAGGGAGA|GGGCACTGTG|360|
|AAATACACCC|TCTCAGGAGA|TGGCGCTGGC|ACCGTTTTTA|CCATTGATGA|ACCACAGGG|420|
|GACATTCATG|CAATAAGGAG|CCTAGATAGA|AAGAGAAAC|CTTTCTACAC|TCTTCGTGCT|480|
|CAGGCTGTGG|ACATAGAAAC|CAGAAAGCCC|CTGGAGCCTG|AATCAGAATT|CATCATCAAA|540|
|GTGCAGGATA|TTAATGATAA|TGAGCCAAAG|TTTTTGGATG|GACCTTATGT|TGCTACTGTT|600|
|CCAGAAATGT|CTCCTGTGGG|TGCATATGTA|CTCCAGGTCA|AGGCCACAGA|TGCAGATGAC|660|
|CCGACCTATG|GAAACAGTGC|CAGAGTCGTT|TACAGCATTC|TTCAGGGACA|ACCTTATTTC|720|
|TCTATTGATC|CAAGACAGG|TGTTATTAGA|ACAGCTTGC|CAAACATGGA|CAGAGAAGTC|780|
|AAAGAACAAT|ATCAAGTACT|CATCCAAGCC|AAGGATATGG|AGGACAGCT|TGGAGGATTA|840|
|GCCGGAACAA|CAATAGTCAA|CATCACTCTC|ACCGATGTCA|ATGACAATCC|ACCTCGATTC|900|
|CCCAAAAGCA|TCTTCCACTT|GAAAGTTCCT|GAGTCTTCCC|CTATTGGTTC|AGCTATTGGA|960|
|AGAATAAGAG|CTGTGGATCC|TGATTTTGGA|CAAAATGCAG|AAATTGAATA|CAATATTGTT|1020|
|CCAGGAGATG|GGGGAAATTT|GTTTGACATC|GTCACAGATG|AGGATACACA|AGAGGGAGTC|1080|
|ATCAAATTGA|AAAAGCCTTT|AGATTTTGAA|ACAAGAAGG|CATACACTTT|CAAAGTTGAG|1140|
|GCTTCCAACC|TTCACCTTGA|CCACCGGTTT|CACTCGGCGG|GCCCTTTCAA|AGACACAGCT|1200|

-continued

```
ACGGTGAAGA TCAGCGTGCT GGACGTAGAT GAGCCACCGG TTTTCAGCAA GCCGCTCTAC      1260
ACCATGGAGG TTTATGAAGA CACTCCGGTA GGGACCATCA TTGGCGCTGT CACTGCTCAA      1320
GACCTGGATG TAGGCAGCGG TGCTGTTAGG TACTTCATAG ATTGGAAGAG TGATGGGGAC      1380
AGCTACTTTA CAATAGATGG AAATGAAGGA ACCATCGCCA CTAATGAATT ACTAGACAGA      1440
GAAAGCACTG CGCAGTATAA TTTCTCCATA ATTGCGAGTA AAGTTAGTAA CCCTTTATTG      1500
ACCAGCAAAG TCAATATACT GATTAATGTC TTAGATGTAA ATGAATTTCC TCCAGAAATA      1560
TCTGTGCCAT ATGAGACAGC CGTGTGTGAA AATGCCAAGC CAGGACAGAT AATTCAGATA      1620
GTCAGTGCTG CAGACCGAGA TCTTTCACCT GCTGGGCAAC AATTCTCCTT TAGATTATCA      1680
CCTGAGGCTG CTATCAAACC AAATTTTACA GTTCGTGACT TCAGAAACAA CACAGCGGGG      1740
ATTGAAACCC GAAGAAATGG ATACAGCCGC AGGCAGCAAG AGTTGTATTT CCTCCCTGTT      1800
GTAATAGAAG ACAGCAGCTA CCCTGTCCAG AGCAGCACAA ACACAATGAC TATTCGAGTC      1860
TGTAGATGTG ACTCTGATGG CACCATCCTG TCTTGTAATG TGGAAGCAAT TTTTCTACCT      1920
GTAGGACTTA GCACTGGGGC GTTGATTGCA ATTCTACTAT GCATTGTTAT ACTCTTAGCC      1980
ATAGTTGTAC TGTATGTAGC ACTGCGAAGG CAGAAGAAAA AGCACACCCT GATGACCTCT      2040
AAAGAAGACA TCAGAGACAA CGTCATCCAT TACGATGATG AAGGAGGTGG GGAGGAAGAT      2100
ACCCAGGCTT TCGACATCGG GGCTCTGAGA AACCCAAAAG TGATTGAGGA GAACAAAATT      2160
CGCAGGGATA TAAAACCAGA CTCTCTCTGT TTACCTCGTC AGAGACCACC CATGGAAGAT      2220
AACACAGACA TAAGGGATTT CATTCATCAA AGGCTACAGG AAAATGATGT AGATCCAACT      2280
GCCCCACCAA TCGATTCACT GGCCACATAT GCCTACGAAG GGAGTGGGTC CGTGGCAGAG      2340
TCCCTCAGCT CTATAGACTC TCTCACCACA GAAGCCGACC AGGACTATGA CTATCTGACA      2400
GACTGGGGAC CCCGCTTTAA AGTCTTGGCA GACATGTTTG CGAAGAAGA GAGTTATAAC      2460
CCTGATAAAG TCACTTAAGG GAGTCGTGGA GGCTAAAATA CAACCGAGAG GGAGATTTT      2520
T                                                                      2521
```

( 2 ) INFORMATION FOR SEQ ID NO:54:

( i ) SEQUENCE CHARACTERISTICS:
        ( A ) LENGTH: 794 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

```
Met Leu Thr Arg Asn Cys Leu Ser Leu Leu Leu Trp Val Leu Phe Asp
 1               5                  10                  15

Gly Gly Leu Leu Thr Pro Leu Gln Pro Gln Pro Gln Gln Thr Leu Ala
                20                  25                  30

Thr Glu Pro Arg Glu Asn Val Ile His Leu Pro Gly Gln Arg Ser His
            35                  40                  45

Phe Gln Arg Val Lys Arg Gly Trp Val Trp Asn Gln Phe Phe Val Leu
        50                  55                  60

Glu Glu Tyr Val Gly Ser Glu Pro Gln Tyr Val Gly Lys Leu His Ser
65                  70                  75                  80

Asp Leu Asp Lys Gly Glu Gly Thr Val Lys Tyr Thr Leu Ser Gly Asp
                85                  90                  95

Gly Ala Gly Thr Val Phe Thr Ile Asp Glu Thr Thr Gly Asp Ile His
                100                 105                 110
```

```
Ala  Ile  Arg  Ser  Leu  Asp  Arg  Glu  Glu  Lys  Pro  Phe  Tyr  Thr  Leu  Arg
          115                 120                      125

Ala  Gln  Ala  Val  Asp  Ile  Glu  Thr  Arg  Lys  Pro  Leu  Glu  Pro  Glu  Ser
     130                 135                      140

Glu  Phe  Ile  Ile  Lys  Val  Gln  Asp  Ile  Asn  Asp  Asn  Glu  Pro  Lys  Phe
145                      150                      155                      160

Leu  Asp  Gly  Pro  Tyr  Val  Ala  Thr  Val  Pro  Glu  Met  Ser  Pro  Val  Gly
                    165                      170                      175

Ala  Tyr  Val  Leu  Gln  Val  Lys  Ala  Thr  Asp  Ala  Asp  Asp  Pro  Thr  Tyr
               180                      185                      190

Gly  Asn  Ser  Ala  Arg  Val  Val  Tyr  Ser  Ile  Leu  Gln  Gly  Gln  Pro  Tyr
          195                      200                      205

Phe  Ser  Ile  Asp  Pro  Lys  Thr  Gly  Val  Ile  Arg  Thr  Ala  Leu  Pro  Asn
210                      215                      220

Met  Asp  Arg  Glu  Val  Lys  Glu  Gln  Tyr  Gln  Val  Leu  Ile  Gln  Ala  Lys
225                      230                      235                      240

Asp  Met  Gly  Gly  Gln  Leu  Gly  Gly  Leu  Ala  Gly  Thr  Thr  Ile  Val  Asn
                    245                      250                      255

Ile  Thr  Leu  Thr  Asp  Val  Asn  Asp  Asn  Pro  Pro  Arg  Phe  Pro  Lys  Ser
               260                      265                      270

Ile  Phe  His  Leu  Lys  Val  Pro  Glu  Ser  Ser  Pro  Ile  Gly  Ser  Gly  Ile
          275                      280                      285

Gly  Arg  Ile  Arg  Ala  Val  Asp  Pro  Asp  Phe  Gly  Gln  Asn  Ala  Glu  Ile
     290                      295                      300

Glu  Tyr  Asn  Ile  Val  Pro  Gly  Asp  Gly  Gly  Asn  Leu  Phe  Asp  Ile  Val
305                      310                      315                      320

Thr  Asp  Glu  Asp  Thr  Gln  Glu  Gly  Val  Ile  Lys  Leu  Lys  Lys  Pro  Leu
                    325                      330                      335

Asp  Phe  Glu  Thr  Lys  Lys  Ala  Tyr  Thr  Phe  Lys  Val  Glu  Ala  Ser  Asn
               340                      345                      350

Leu  His  Leu  Asp  His  Arg  Phe  His  Ser  Ala  Gly  Pro  Phe  Lys  Asp  Thr
          355                      360                      365

Ala  Thr  Val  Lys  Ile  Ser  Val  Leu  Asp  Val  Asp  Glu  Pro  Pro  Val  Phe
     370                      375                      380

Ser  Lys  Pro  Leu  Tyr  Thr  Met  Glu  Val  Tyr  Glu  Asp  Thr  Pro  Val  Gly
385                      390                      395                      400

Thr  Ile  Ile  Gly  Ala  Val  Thr  Ala  Gln  Asp  Leu  Asp  Val  Gly  Ser  Gly
                    405                      410                      415

Ala  Val  Arg  Tyr  Phe  Ile  Asp  Trp  Lys  Ser  Asp  Gly  Asp  Ser  Tyr  Phe
               420                      425                      430

Thr  Ile  Asp  Gly  Asn  Glu  Gly  Thr  Ile  Ala  Thr  Asn  Glu  Leu  Leu  Asp
          435                      440                      445

Arg  Glu  Ser  Thr  Ala  Gln  Tyr  Asn  Phe  Ser  Ile  Ile  Ala  Ser  Lys  Val
     450                      455                      460

Ser  Asn  Pro  Leu  Leu  Thr  Ser  Lys  Val  Asn  Ile  Leu  Ile  Asn  Val  Leu
465                      470                      475                      480

Asp  Val  Asn  Glu  Phe  Pro  Pro  Glu  Ile  Ser  Val  Pro  Tyr  Glu  Thr  Ala
                    485                      490                      495

Val  Cys  Glu  Asn  Ala  Lys  Pro  Gly  Gln  Ile  Ile  Gln  Ile  Val  Ser  Ala
               500                      505                      510

Ala  Asp  Arg  Asp  Leu  Ser  Pro  Ala  Gly  Gln  Gln  Phe  Ser  Phe  Arg  Leu
          515                      520                      525

Ser  Pro  Glu  Ala  Ala  Ile  Lys  Pro  Asn  Phe  Thr  Val  Arg  Asp  Phe  Arg
     530                      535                      540
```

|        |     |     |     |     |     |     |     |     |     |     |     |     |     |     |     |
|---|---|---|---|---|---|---|---|---|---|---|---|---|---|---|---|
| Asn<br>545 | Asn | Thr | Ala | Gly | Ile<br>550 | Glu | Thr | Arg | Arg | Asn<br>555 | Gly | Tyr | Ser | Arg | Arg<br>560 |
| Gln | Gln | Glu | Leu | Tyr<br>565 | Phe | Leu | Pro | Val | Val<br>570 | Ile | Glu | Asp | Ser | Ser<br>575 | Tyr |
| Pro | Val | Gln | Ser<br>580 | Ser | Thr | Asn | Thr | Met<br>585 | Thr | Ile | Arg | Val | Cys<br>590 | Arg | Cys |
| Asp | Ser | Asp<br>595 | Gly | Thr | Ile | Leu | Ser<br>600 | Cys | Asn | Val | Glu | Ala<br>605 | Ile | Phe | Leu |
| Pro | Val<br>610 | Gly | Leu | Ser | Thr | Gly<br>615 | Ala | Leu | Ile | Ala | Ile<br>620 | Leu | Leu | Cys | Ile |
| Val<br>625 | Ile | Leu | Leu | Ala | Ile<br>630 | Val | Val | Leu | Tyr | Val<br>635 | Ala | Leu | Arg | Arg | Gln<br>640 |
| Lys | Lys | Lys | His | Thr<br>645 | Leu | Met | Thr | Ser | Lys<br>650 | Glu | Asp | Ile | Arg | Asp<br>655 | Asn |
| Val | Ile | His | Tyr<br>660 | Asp | Asp | Glu | Gly | Gly<br>665 | Gly | Glu | Glu | Asp | Thr<br>670 | Gln | Ala |
| Phe | Asp | Ile<br>675 | Gly | Ala | Leu | Arg | Asn<br>680 | Pro | Lys | Val | Ile | Glu<br>685 | Glu | Asn | Lys |
| Ile | Arg<br>690 | Arg | Asp | Ile | Lys | Pro<br>695 | Asp | Ser | Leu | Cys | Leu<br>700 | Pro | Arg | Gln | Arg |
| Pro<br>705 | Pro | Met | Glu | Asp | Asn<br>710 | Thr | Asp | Ile | Arg | Asp<br>715 | Phe | Ile | His | Gln | Arg<br>720 |
| Leu | Gln | Glu | Asn | Asp<br>725 | Val | Asp | Pro | Thr | Ala<br>730 | Pro | Pro | Ile | Asp | Ser<br>735 | Leu |
| Ala | Thr | Tyr | Ala<br>740 | Tyr | Glu | Gly | Ser | Gly<br>745 | Ser | Val | Ala | Glu | Ser<br>750 | Leu | Ser |
| Ser | Ile | Asp<br>755 | Ser | Leu | Thr | Thr | Glu<br>760 | Ala | Asp | Gln | Asp | Tyr<br>765 | Asp | Tyr | Leu |
| Thr | Asp<br>770 | Trp | Gly | Pro | Arg | Phe<br>775 | Lys | Val | Val | Ala | Asp<br>780 | Met | Phe | Gly | Glu |
| Glu<br>785 | Glu | Ser | Tyr | Asn | Pro<br>790 | Asp | Lys | Val | Thr | | | | | | |

( 2 ) INFORMATION FOR SEQ ID NO:55:

( i ) SEQUENCE CHARACTERISTICS:
      ( A ) LENGTH: 2690 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:55:

```
CTTCAAGGTT TTGCTGACTC AGTCTGGTAG TCAGAGTCTG CAGGAGAAGA CAGTTCAAGG        60
CAGGGCCTGG AGGATTGGAT CAGTTTAGGG ACAGGTCAAA GGCTGGCTTA GAGACCTTAG       120
AGGCAGGTTG CTTGGGTCGT TGAATGCTAG TCTGGTCCTG AGAGCCCTTT TCTCTGGCAA       180
CTGTGGACTC AGAGCTAACC AATTGTAGTT GGCAGTGGGG GTGAAGGGTG ATCCAGAGGC       240
CTGAGCTGCA GAGGGCACAA GAGAGAAAAG ATGTCTTAGA AAGAGCTTTG AGAACATGCC       300
TTGGCTGCTG GCAGGGACCT TGGATGGGGT AGTCTACACC CGGAAGTGCC TGCCTGCCAT       360
CCTCTAGTGG CTGCCTTGCA AAATATGCTC AGTGCAGCCG CGTGCATGAA TGAAAACGCC       420
GCCGGGCGCT TCTAGTCGGA CAAAATGCAG CCGAGAACTC CGCTCGTTCT GTGCGTTCTC       480
CTGTCCCAGG TGCTGCTGCT AACATCTGCA GAAGATTTGG ACTGCACTCC TGGATTTCAG       540
```

| | | | | | |
|---|---|---|---|---|---|
| CAGAAAGTGT | TCCATATCAA | TCAGCCAGCT | GAATTCATTG | AGGACCAGTC | AATTCTAAAC | 600 |
| TTGACCTTCA | GTGACTGTAA | GGGAAACGAC | AAGCTACGCT | ATGAGGTCTC | GAGCCCATAC | 660 |
| TTCAAGGTGA | ACAGCGATGG | CGGCTTAGTT | GCTCTGAGAA | ACATAACTGC | AGTGGGCAAA | 720 |
| ACTCTGTTCG | TCCATGCACG | GACCCCCCAT | GCGGAAGATA | TGGCAGAACT | CGTGATTGTC | 780 |
| GGGGGGAAAG | ACATCCAGGG | CTCCTTGCAG | GATATATTTA | AATTTGCAAG | AACTTCTCCT | 840 |
| GTCCCAAGAC | AAAAGAGGTC | CATTGTGGTA | TCTCCCATTT | TAATTCCAGA | GAATCAGAGA | 900 |
| CAGCCTTTCC | CAAGAGATGT | TGGCAAGGTA | GTCGATAGTG | ACAGGCCAGA | AAGGTCCAAG | 960 |
| TTCCGGCTCA | CTGGAAAGGG | AGTGGATCAA | GAGCCTAAAG | GAATTTCAG | AATCAATGAG | 1020 |
| AACACAGGGA | GCGTCTCCGT | GACACGGACC | TTGGACAGAG | AAGTAATCGC | TGTTTATCAA | 1080 |
| CTATTTGTGG | AGACCACTGA | TGTCAATGGC | AAAACTCTCG | AGGGGCCGGT | GCCTCTGGAA | 1140 |
| GTCATTGTGA | TTGATCAGAA | TGACAACCGA | CCGATCTTTC | GGGAAGGCCC | CTACATCGGC | 1200 |
| CACGTCATGG | AAGGGTCACC | CACAGGCACC | ACAGTGATGC | GGATGACAGC | CTTTGATGCA | 1260 |
| GATGACCCAG | CCACCGATAA | TGCCCTCCTG | CGGTATAATA | TCCGTCAACA | GACGCCTGAC | 1320 |
| AAGCCATCTC | CCAACATGTT | CTACATCGAT | CCTGAGAAAG | GAGACATTGT | CACTGTTGTG | 1380 |
| TCACCTGCGC | TGCTGGACCG | AGAGACTCTG | GAAAATCCCA | AGTATGAACT | GATCATCGAG | 1440 |
| GCTCAAGATA | TGGCTGGACT | GGATGTTGGA | TTAACAGGCA | CGGCCACAGC | CACGATCATG | 1500 |
| ATCGATGACA | AAAATGATCA | CTCACCAAAA | TTCACCAAGA | AAGAGTTTCA | AGCCACAGTC | 1560 |
| GAGGAAGGAG | CTGTGGGAGT | TATTGTCAAT | TTGACAGTTG | AAGATAAGGA | TGACCCCACC | 1620 |
| ACAGGTGCAT | GGAGGGCTGC | CTACACCATC | ATCAACGGAA | ACCCCGGGCA | GAGCTTTGAA | 1680 |
| ATCCACACCA | ACCCTCAAAC | CAACGAAGGG | ATGCTTTCTG | TTGTCAAACC | ATTGGACTAT | 1740 |
| GAAATTTCTG | CCTTCCACAC | CCTGCTGATC | AAAGTGGAAA | ATGAAGACCC | ACTCGTACCC | 1800 |
| GACGTCTCCT | ACGGCCCCAG | CTCCACAGCC | ACCGTCCACA | TCACTGTCCT | GGATGTCAAC | 1860 |
| GAGGGCCCAG | TCTTCTACCC | AGACCCCATG | ATGGTGACCA | GGCAGGAGGA | CCTCTCTGTG | 1920 |
| GGCAGCGTGC | TGCTGACAGT | GAATGCCACG | GACCCCGACT | CCCTGCAGCA | TCAAACCATC | 1980 |
| AGGTATTCTG | TTTACAAGGA | CCCAGCAGGT | TGGCTGAATA | TTAACCCCAT | CAATGGGACT | 2040 |
| GTTGACACCA | CAGCTGTGCT | GGACCGTGAG | TCCCCATTTG | TCGACAACAG | CGTGTACACT | 2100 |
| GCTCTCTTCC | TGGCAATTGA | CAGTGGCAAC | CCTCCGCTA | CGGGCACTGG | GACTTTGCTG | 2160 |
| ATAACCCTGG | AGGACGTGAA | TGACAATGCC | CCGTTCATTT | ACCCCACAGT | AGCTGAAGTC | 2220 |
| TGTGATGATG | CCAAAAACCT | CAGTGTAGTC | ATTTTGGGAG | CATCAGATAA | GGATCTTCAC | 2280 |
| CCGAATACAG | ATCCTTTCAA | ATTTGAAATC | CACAAACAAG | CTGTTCCTGA | TAAAGTCTGG | 2340 |
| AAGATCTCCA | AGATCAACAA | TACACACGCC | CTGGTAAGCC | TTCTTCAAAA | TCTGAACAAA | 2400 |
| GCAAACTACA | ACCTGCCCAT | CATGGTGACA | GATTCAGGGA | ACCACCCAT | GACGAATATC | 2460 |
| ACAGATCTCA | GGGTACAAGT | GTGCTCCTGC | AGGAATTCCA | AAGTGGACTG | CAACGCGGCG | 2520 |
| GGGGCCCTGC | GCTTCAGCCT | GCCCTCAGTC | CTGCTCCTCA | GCCTCTTCAG | CTTAGCTTGT | 2580 |
| CTGTGAGAAC | TCCTGACGTC | TGAAGCTTGA | CTCCCAAGTT | TCCATAGCAA | CAGGAAAAAA | 2640 |
| AAAAAATCTA | TCCAAATCTG | AAGATTGCGG | TTTACAGCTA | TCGAACTTCG | | 2690 |

( 2 ) INFORMATION FOR SEQ ID NO:56:

( i ) SEQUENCE CHARACTERISTICS:
        ( A ) LENGTH: 713 amino acids
        ( B ) TYPE: amino acid
        ( D ) TOPOLOGY: linear (i i) MOLECULE TYPE: protein (x i) SEQUENCE DESCRIPTION: SEQ ID NO:56:

| Met | Gln | Pro | Arg | Thr | Pro | Leu | Val | Leu | Cys | Val | Leu | Leu | Ser | Gln | Val |
|---|---|---|---|---|---|---|---|---|---|---|---|---|---|---|---|
| 1 | | | | 5 | | | | | 10 | | | | | 15 | |

| Leu | Leu | Leu | Thr | Ser | Ala | Glu | Asp | Leu | Asp | Cys | Thr | Pro | Gly | Phe | Gln |
|---|---|---|---|---|---|---|---|---|---|---|---|---|---|---|---|
| | | | 20 | | | | 25 | | | | | 30 | | | |

| Gln | Lys | Val | Phe | His | Ile | Asn | Gln | Pro | Ala | Glu | Phe | Ile | Glu | Asp | Gln |
|---|---|---|---|---|---|---|---|---|---|---|---|---|---|---|---|
| | | 35 | | | | | 40 | | | | | 45 | | | |

| Ser | Ile | Leu | Asn | Leu | Thr | Phe | Ser | Asp | Cys | Lys | Gly | Asn | Asp | Lys | Leu |
|---|---|---|---|---|---|---|---|---|---|---|---|---|---|---|---|
| | 50 | | | | | 55 | | | | | 60 | | | | |

| Arg | Tyr | Glu | Val | Ser | Ser | Pro | Tyr | Phe | Lys | Val | Asn | Ser | Asp | Gly | Gly |
|---|---|---|---|---|---|---|---|---|---|---|---|---|---|---|---|
| 65 | | | | | 70 | | | | | 75 | | | | | 80 |

| Leu | Val | Ala | Leu | Arg | Asn | Ile | Thr | Ala | Val | Gly | Lys | Thr | Leu | Phe | Val |
|---|---|---|---|---|---|---|---|---|---|---|---|---|---|---|---|
| | | | | 85 | | | | | 90 | | | | | 95 | |

| His | Ala | Arg | Thr | Pro | His | Ala | Glu | Asp | Met | Ala | Glu | Leu | Val | Ile | Val |
|---|---|---|---|---|---|---|---|---|---|---|---|---|---|---|---|
| | | | 100 | | | | 105 | | | | | 110 | | | |

| Gly | Gly | Lys | Asp | Ile | Gln | Gly | Ser | Leu | Gln | Asp | Ile | Phe | Lys | Phe | Ala |
|---|---|---|---|---|---|---|---|---|---|---|---|---|---|---|---|
| | | 115 | | | | | 120 | | | | | 125 | | | |

| Arg | Thr | Ser | Pro | Val | Pro | Arg | Gln | Lys | Arg | Ser | Ile | Val | Val | Ser | Pro |
|---|---|---|---|---|---|---|---|---|---|---|---|---|---|---|---|
| 130 | | | | | 135 | | | | | 140 | | | | | |

| Ile | Leu | Ile | Pro | Glu | Asn | Gln | Arg | Gln | Pro | Phe | Pro | Arg | Asp | Val | Gly |
|---|---|---|---|---|---|---|---|---|---|---|---|---|---|---|---|
| 145 | | | | | 150 | | | | | 155 | | | | | 160 |

| Lys | Val | Val | Asp | Ser | Asp | Arg | Pro | Glu | Arg | Ser | Lys | Phe | Arg | Leu | Thr |
|---|---|---|---|---|---|---|---|---|---|---|---|---|---|---|---|
| | | | | 165 | | | | | 170 | | | | | 175 | |

| Gly | Lys | Gly | Val | Asp | Gln | Glu | Pro | Lys | Gly | Ile | Phe | Arg | Ile | Asn | Glu |
|---|---|---|---|---|---|---|---|---|---|---|---|---|---|---|---|
| | | | 180 | | | | | 185 | | | | | 190 | | |

| Asn | Thr | Gly | Ser | Val | Ser | Val | Thr | Arg | Thr | Leu | Asp | Arg | Glu | Val | Ile |
|---|---|---|---|---|---|---|---|---|---|---|---|---|---|---|---|
| | | 195 | | | | | 200 | | | | | 205 | | | |

| Ala | Val | Tyr | Gln | Leu | Phe | Val | Glu | Thr | Thr | Asp | Val | Asn | Gly | Lys | Thr |
|---|---|---|---|---|---|---|---|---|---|---|---|---|---|---|---|
| | 210 | | | | | 215 | | | | | 220 | | | | |

| Leu | Glu | Gly | Pro | Val | Pro | Leu | Glu | Val | Ile | Val | Ile | Asp | Gln | Asn | Asp |
|---|---|---|---|---|---|---|---|---|---|---|---|---|---|---|---|
| 225 | | | | | 230 | | | | | 235 | | | | | 240 |

| Asn | Arg | Pro | Ile | Phe | Arg | Glu | Gly | Pro | Tyr | Ile | Gly | His | Val | Met | Glu |
|---|---|---|---|---|---|---|---|---|---|---|---|---|---|---|---|
| | | | | 245 | | | | | 250 | | | | | 255 | |

| Gly | Ser | Pro | Thr | Gly | Thr | Thr | Val | Met | Arg | Met | Thr | Ala | Phe | Asp | Ala |
|---|---|---|---|---|---|---|---|---|---|---|---|---|---|---|---|
| | | | 260 | | | | | 265 | | | | | 270 | | |

| Asp | Asp | Pro | Ala | Thr | Asp | Asn | Ala | Leu | Leu | Arg | Tyr | Asn | Ile | Arg | Gln |
|---|---|---|---|---|---|---|---|---|---|---|---|---|---|---|---|
| | | 275 | | | | | 280 | | | | | 285 | | | |

| Gln | Thr | Pro | Asp | Lys | Pro | Ser | Pro | Asn | Met | Phe | Tyr | Ile | Asp | Pro | Glu |
|---|---|---|---|---|---|---|---|---|---|---|---|---|---|---|---|
| | 290 | | | | | 295 | | | | | 300 | | | | |

| Lys | Gly | Asp | Ile | Val | Thr | Val | Val | Ser | Pro | Ala | Leu | Leu | Asp | Arg | Glu |
|---|---|---|---|---|---|---|---|---|---|---|---|---|---|---|---|
| 305 | | | | | 310 | | | | | 315 | | | | | 320 |

| Thr | Leu | Glu | Asn | Pro | Lys | Tyr | Glu | Leu | Ile | Ile | Glu | Ala | Gln | Asp | Met |
|---|---|---|---|---|---|---|---|---|---|---|---|---|---|---|---|
| | | | | 325 | | | | | 330 | | | | | 335 | |

| Ala | Gly | Leu | Asp | Val | Gly | Leu | Thr | Gly | Thr | Ala | Thr | Ala | Thr | Ile | Met |
|---|---|---|---|---|---|---|---|---|---|---|---|---|---|---|---|
| | | | 340 | | | | | 345 | | | | | 350 | | |

| Ile | Asp | Asp | Lys | Asn | Asp | His | Ser | Pro | Lys | Phe | Thr | Lys | Lys | Glu | Phe |
|---|---|---|---|---|---|---|---|---|---|---|---|---|---|---|---|
| | | 355 | | | | | 360 | | | | | 365 | | | |

| Gln | Ala | Thr | Val | Glu | Glu | Gly | Ala | Val | Gly | Val | Ile | Val | Asn | Leu | Thr |
|---|---|---|---|---|---|---|---|---|---|---|---|---|---|---|---|
| | 370 | | | | | 375 | | | | | 380 | | | | |

| Val | Glu | Asp | Lys | Asp | Asp | Pro | Thr | Thr | Gly | Ala | Trp | Arg | Ala | Ala | Tyr |
|---|---|---|---|---|---|---|---|---|---|---|---|---|---|---|---|
| 385 | | | | | 390 | | | | | 395 | | | | | 400 |

| Thr | Ile | Ile | Asn | Gly | Asn | Pro | Gly | Gln | Ser | Phe | Glu | Ile | His | Thr | Asn |
|---|---|---|---|---|---|---|---|---|---|---|---|---|---|---|---|

|  |  |  | 405 |  |  |  |  | 410 |  |  |  | 415 |  |  |
|---|---|---|---|---|---|---|---|---|---|---|---|---|---|---|
| Pro | Gln | Thr | Asn 420 | Glu | Gly | Met | Leu | Ser 425 | Val | Val | Lys | Pro | Leu 430 | Asp | Tyr |
| Glu | Ile | Ser 435 | Ala | Phe | His | Thr | Leu 440 | Leu | Ile | Lys | Val | Glu 445 | Asn | Glu | Asp |
| Pro | Leu 450 | Val | Pro | Asp | Val | Ser 455 | Tyr | Gly | Pro | Ser | Ser 460 | Thr | Ala | Thr | Val |
| His 465 | Ile | Thr | Val | Leu | Asp 470 | Val | Asn | Glu | Gly | Pro 475 | Val | Phe | Tyr | Pro | Asp 480 |
| Pro | Met | Met | Val | Thr 485 | Arg | Gln | Glu | Asp | Leu 490 | Ser | Val | Gly | Ser | Val 495 | Leu |
| Leu | Thr | Val | Asn 500 | Ala | Thr | Asp | Pro | Asp 505 | Ser | Leu | Gln | His | Gln 510 | Thr | Ile |
| Arg | Tyr | Ser 515 | Val | Tyr | Lys | Asp | Pro 520 | Ala | Gly | Trp | Leu | Asn 525 | Ile | Asn | Pro |
| Ile | Asn 530 | Gly | Thr | Val | Asp | Thr 535 | Thr | Ala | Val | Leu | Asp 540 | Arg | Glu | Ser | Pro |
| Phe 545 | Val | Asp | Asn | Ser | Val 550 | Tyr | Thr | Ala | Leu | Phe 555 | Leu | Ala | Ile | Asp | Ser 560 |
| Gly | Asn | Pro | Pro | Ala 565 | Thr | Gly | Thr | Gly | Thr 570 | Leu | Leu | Ile | Thr | Leu 575 | Glu |
| Asp | Val | Asn | Asp 580 | Asn | Ala | Pro | Phe | Ile 585 | Tyr | Pro | Thr | Val | Ala 590 | Glu | Val |
| Cys | Asp | Asp 595 | Ala | Lys | Asn | Leu | Ser 600 | Val | Val | Ile | Leu | Gly 605 | Ala | Ser | Asp |
| Lys | Asp 610 | Leu | His | Pro | Asn | Thr 615 | Asp | Pro | Phe | Lys | Phe 620 | Glu | Ile | His | Lys |
| Gln 625 | Ala | Val | Pro | Asp | Lys 630 | Val | Trp | Lys | Ile | Ser 635 | Lys | Ile | Asn | Asn | Thr 640 |
| His | Ala | Leu | Val | Ser 645 | Leu | Leu | Gln | Asn | Leu 650 | Asn | Lys | Ala | Asn | Tyr 655 | Asn |
| Leu | Pro | Ile | Met 660 | Val | Thr | Asp | Ser | Gly 665 | Lys | Pro | Pro | Met | Thr 670 | Asn | Ile |
| Thr | Asp | Leu 675 | Arg | Val | Gln | Val | Cys 680 | Ser | Cys | Arg | Asn | Ser 685 | Lys | Val | Asp |
| Cys | Asn 690 | Ala | Ala | Gly | Ala | Leu 695 | Arg | Phe | Ser | Leu | Pro 700 | Ser | Val | Ile | Leu |
| Leu 705 | Ser | Leu | Phe | Ser | Leu 710 | Ala | Cys | Leu |  |  |  |  |  |  |  |